(12) United States Patent
Lee et al.

(10) Patent No.: US 11,339,196 B2
(45) Date of Patent: May 24, 2022

(54) METHOD USING EXPRESSION OF LIN28 FOR PREPARING STEM CELLS HAVING EXCELLENT RENEWAL ABILITY AND THERAPEUTIC CAPACITY

(71) Applicant: INDUSTRY-UNIVERSITY COOPERATION FOUNDATION HANYANG UNIVERSITY, Seoul (KR)

(72) Inventors: Sang-Hun Lee, Seoul (KR); Yong Hee Rhee, Seoul (KR); Chang-Hwan Park, Seoul (KR); Mi-Yoon Chang, Gyeonggi-do (KR); Yanuar Alan Sulistio, Seoul (KR); Ji Yun Ko, Gyeonggi-do (KR)

(73) Assignee: Industry-University Cooperation Foundation Hanyang University, Seoul (KR)

( * ) Notice: Subject to any disclaimer, the term of this patent is extended or adjusted under 35 U.S.C. 154(b) by 230 days.

(21) Appl. No.: 16/035,318

(22) Filed: Jul. 13, 2018

(65) Prior Publication Data
US 2019/0010197 A1     Jan. 10, 2019

Related U.S. Application Data

(63) Continuation-in-part of application No. PCT/KR2017/000504, filed on Jan. 13, 2017.

(30) Foreign Application Priority Data

Jan. 14, 2016 (KR) .................. 10-2016-0004877

(51) Int. Cl.
| | | |
|---|---|---|
| C07K 14/47 | (2006.01) | |
| A61K 48/00 | (2006.01) | |
| A61K 35/30 | (2015.01) | |
| A61K 35/761 | (2015.01) | |
| C12N 15/861 | (2006.01) | |
| C12N 5/077 | (2010.01) | |
| C12N 5/0775 | (2010.01) | |
| A61K 35/28 | (2015.01) | |
| A61K 35/33 | (2015.01) | |
| A61K 35/34 | (2015.01) | |
| C12N 5/0797 | (2010.01) | |

(52) U.S. Cl.
CPC .......... *C07K 14/4705* (2013.01); *A61K 35/28* (2013.01); *A61K 35/30* (2013.01); *A61K 35/33* (2013.01); *A61K 35/34* (2013.01); *A61K 35/761* (2013.01); *A61K 48/00* (2013.01); *C12N 5/0623* (2013.01); *C12N 5/0654* (2013.01); *C12N 5/0656* (2013.01); *C12N 5/0658* (2013.01); *C12N 5/0662* (2013.01); *C12N 5/0663* (2013.01); *C12N 15/861* (2013.01); *C12N 2501/608* (2013.01); *C12N 2506/1353* (2013.01); *C12N 2510/00* (2013.01)

(58) Field of Classification Search
CPC .. C07K 14/4705; A61K 35/761; A61K 35/28; A61K 35/33; A61K 35/34; A61K 48/00; A61K 35/30; A61K 48/005; C12N 15/861; C12N 5/0663; C12N 5/0658; C12N 5/0656; C12N 2506/1353; C12N 2501/608; C12N 2510/00; C12N 2710/10141; C12N 2800/107; C12N 5/0654; C12N 5/0623; C12N 5/0662
See application file for complete search history.

(56) References Cited

U.S. PATENT DOCUMENTS

| | | | | |
|---|---|---|---|---|
| 6,583,121 B1 * | 6/2003 | Johnston | .............. | C07K 14/005 514/44 R |
| 2008/0254004 A1 * | 10/2008 | Terskikh | .............. | C12N 5/0618 424/93.7 |

FOREIGN PATENT DOCUMENTS

| | | | | |
|---|---|---|---|---|
| KR | 10-2014-0121787 | 10/2014 | | |
| WO | 2009/048932 | 4/2009 | | |
| WO | 2012/135081 | 10/2012 | | |
| WO | 2013/126605 | 8/2013 | | |
| WO | WO-2013123607 A1 * | 8/2013 | ........... | C12N 5/0056 |

OTHER PUBLICATIONS

Copley et al. "The Lin28b-let-7-Hmga2 axis determines the higher self-renewal potential of fetal haematopoietic stem cells." Nature Cell Biology vol. 15, pp. 916-925(2013) (Year: 2013).*
Balzer et al. "LIN28 alters cell fate succession and acts independently of the let-7 microRNA during neurogliogenesis in vitro." Development . Mar. 2010;137(6):891-900. (Year: 2010).*
Cimadamore et al., "SOX2-LIN28/let-7 pathway regulates proliferation and neurogenesis in neural precursors", PNAS, 2013, Published online Jul. 24, 2013, E3017-E3026, www.pnas.org/cgi/doi/10.1073/pnas.1220176110.

(Continued)

*Primary Examiner* — Titilayo Moloye
(74) *Attorney, Agent, or Firm* — Adsero IP

(57) ABSTRACT

The present invention relates to a cell therapeutic agent comprising a stem cell expressing Lin28, a pharmaceutical composition comprising a stem cell expressing Lin28 for the prevention or treatment of a neurological disorder, a bone disorder, a muscular system disorder, an epithelium-related disorder or a blood-related disorder, and a method for treating a neurological disorder, a bone disorder, a muscular system disorder, an epithelium-related disorder or a blood-related disorder using the composition. A stem cell excellent in terms of differentiation potency to various tissue cells and renewal ability can be prepared by introducing Lin28, which regulates an embryonic development procedure, or a vector expressing Lin28 during stem cell culturing, and by culturing the cell.

1 Claim, 44 Drawing Sheets
Specification includes a Sequence Listing.

(56) References Cited

OTHER PUBLICATIONS

Oka et al., "293FT cells transduced with four transcription factors (OCT4, SOX2, NANOG, and LIN28) generate aberrant ES-like cells", Journal of Stem Cells & Regenerative Medicine, vol. 6, No. 3, 2010, pp. 149-156.
Shyh-Chang et al., "Lin28: Primal Regulator of Growth and Metabolism in Stem Cells", Cell Stem Cell 12, Apr. 4, 2013, 395-406.
Yang et al., "Lin28 promotes the proliferative capacity of neural progenitor cells in brain development", Development (2015) 142, 1616-1627.
Balzer et al., "LIN28 alters cell fate succession and acts independently of the let-7 microRNA during neurogliogenesis in vitro", Development and Stem Cells, v. 137, pp. 891-600 (2010), XP-002792817.
Bhuiyan et al., "Expression of Exogenous LIN28 Contributes to Proliferation and Survival of Mouse Primary Cortical Neurons In Vitro"., Neuroscience 248 (2013) 448-458.
European Search Report—Supplementary—for EP 17738694.3, dated Jul. 24, 2019, 8 pages.
Jang et al., "Persistent Lin28 Expression Impairs Neurite Outgrowth and Cognitive Function in the Developing Mouse Neocortex", Molecular Neurobiology (2019) 56:3780-3795.
Liu et al., "Lin28 Induces Epithelial-to-Mesenchymal Transition and Stemness via Downregulation of Let-7a in Breast Cancer Cells", PLOS ONE, Dec. 2013, vol. 8, Issue 12, 14 pages.
Rhee et al., "LIN28A enhances the therapeutic potential of cultured neural stem cells in a Parkinson's disease model", BRAIN 2016: 139, 18 pages.
Antonchuk et al., "*HOXB4*-Induced Expansion of Adult Hematopoietic Stem Cells Ex Vivo", Cell, vol. 109, pp. 39-45, Apr. 5, 2002.
Chaudhuri et al., "Oncomir miR-125b regulates hematopoiesis by targeting the gene Lin28A", PNAS, vol. 109, No. 11, pp. 4233-4238, Mar. 13, 2012.
Iscove et al., "Hematopoietic stem cells expand during serial transplantation in vivo without apparent exhaustion", Current Biology, vol. 7, No. 10, pp. 805-808, 1997.
Pawliuk et al., "Evidence of Both Ontogeny and Transplant Dose-Regulated Expansion of Hematopoietic stem Cells In Vivo", Blood, vol. 88, No. 8, pp. 2852-2858 Oct. 15, 1996.
Sauvageau et al., "In vitro and in vivo expansion of hematopoietic stem cells", Oncogene, vol. 23, pp. 7223-7232, 2004.
Sauvageau et al., "Overexpression of *HOXB4* in hematopoietic cells causes the selective expansion of more primitive populations in vitro and in vivo", Genes & Development, vol. 9, pp. 1753-1765, 1995.
Thorsteinsdottir et al., "Enhanced In Vivo Regenerative Potential of *HOXB4*-Transduced Hematopoietic stem Cells With Regulation of Their Pool Size", Blood, vol. 94, No. 8, pp. 2605-2612, Oct. 15, 1999.
Walasek, Marta Anna, "Hematopoietic stem cell expansion", Groningen: s.n., 2012.

* cited by examiner

[FIG. 1A]
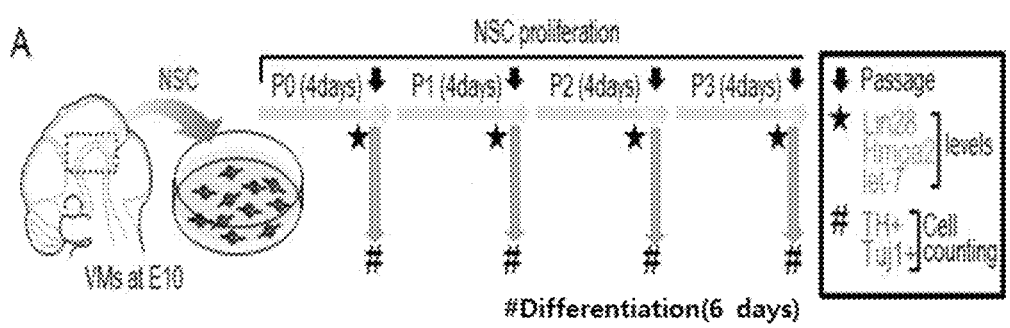

[FIG. 1B]
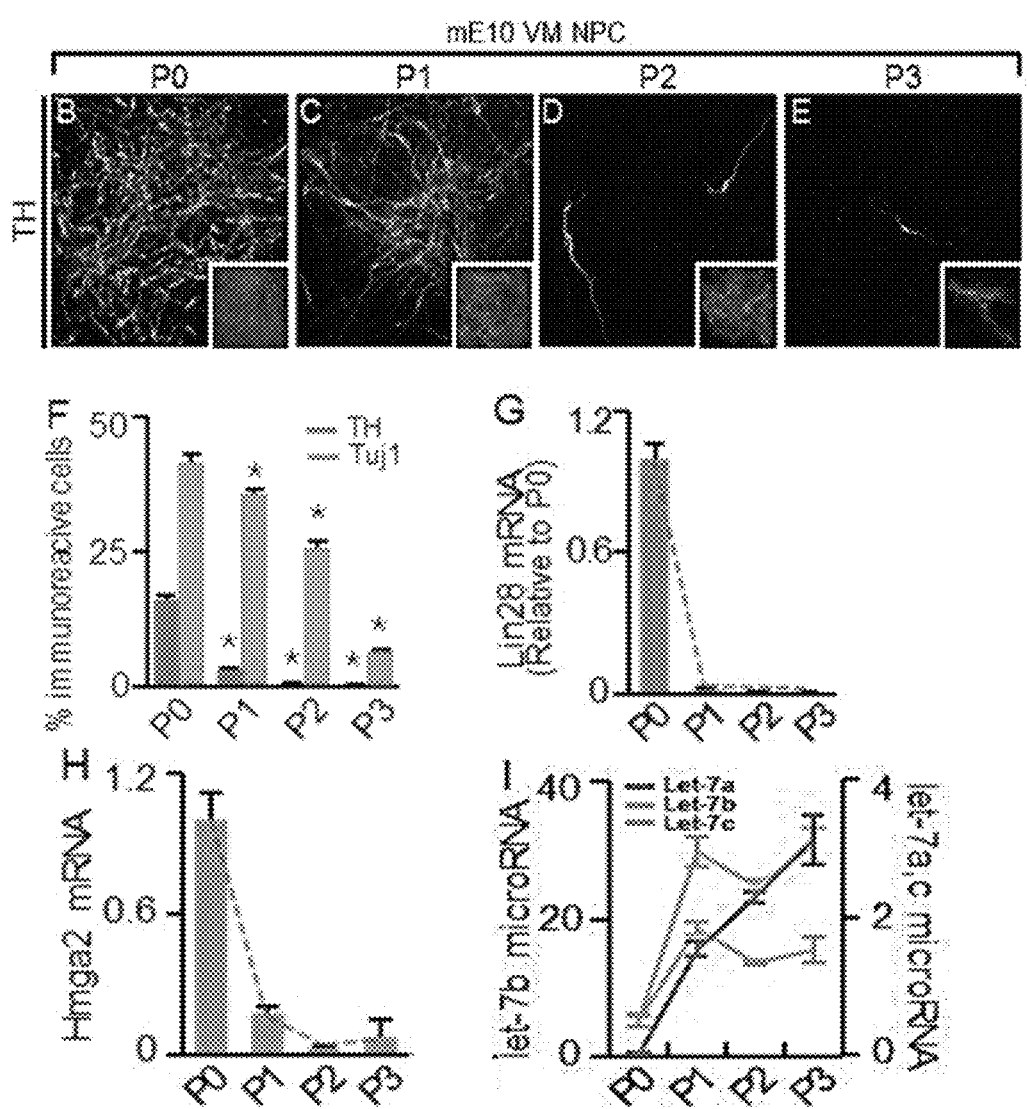

[FIG. 2A]
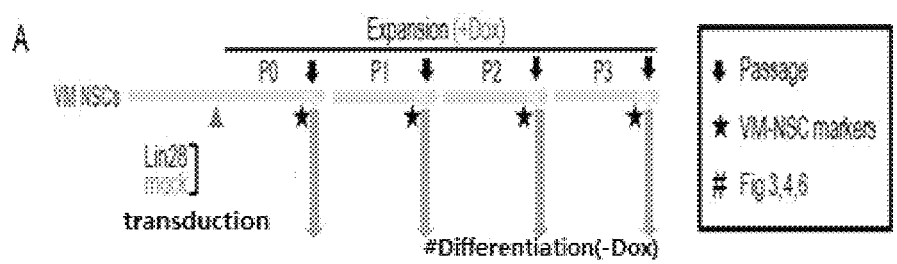
[FIG. 2B]
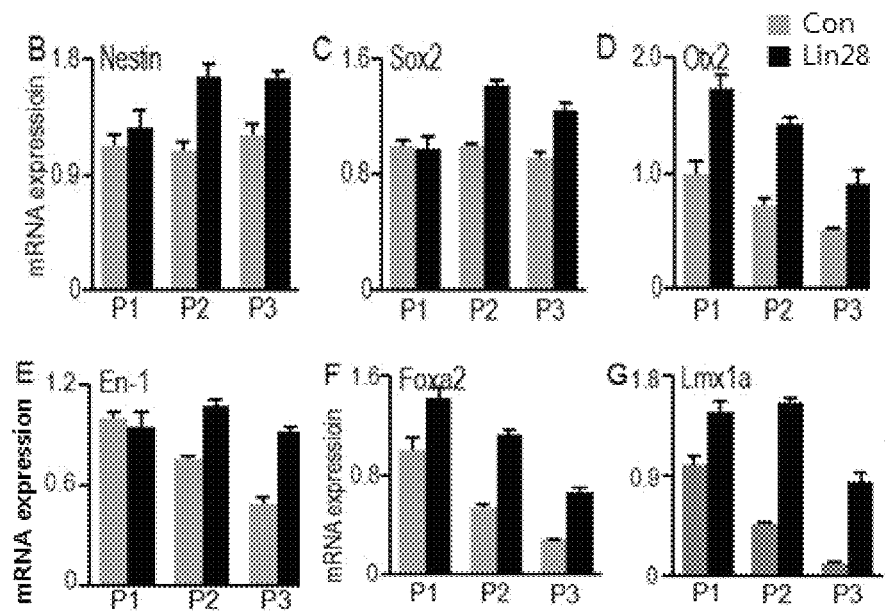

[FIG. 2C]
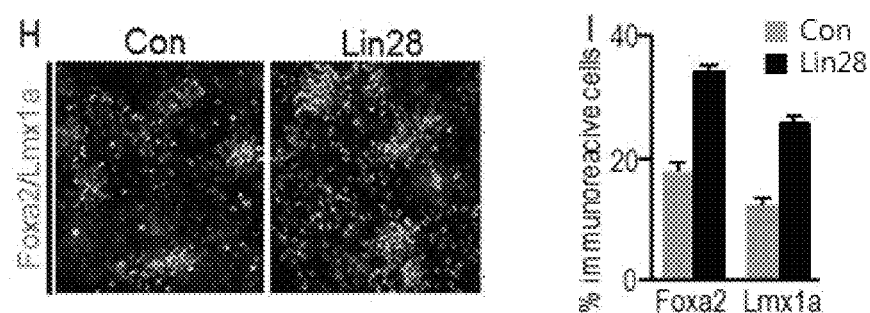

[FIG. 3A]
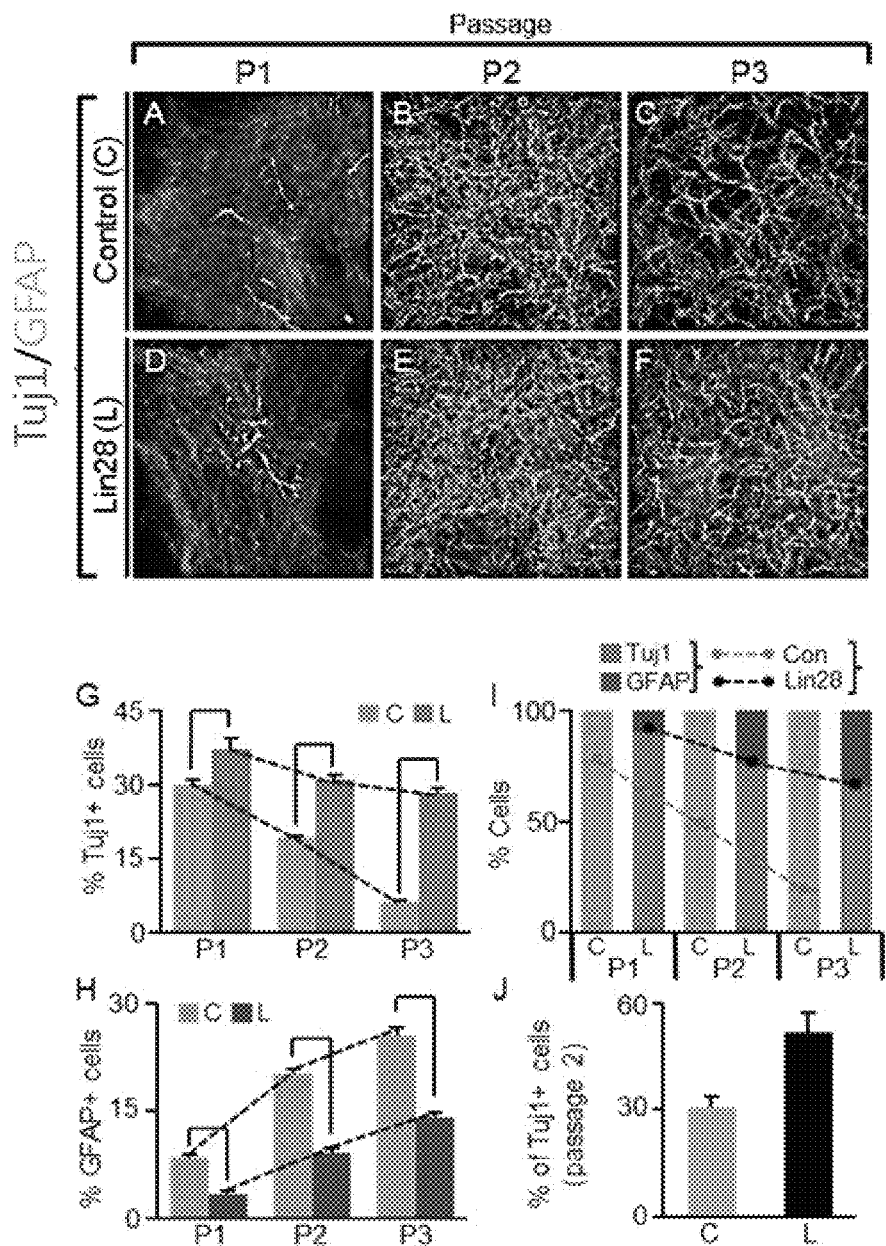

[FIG. 3B]
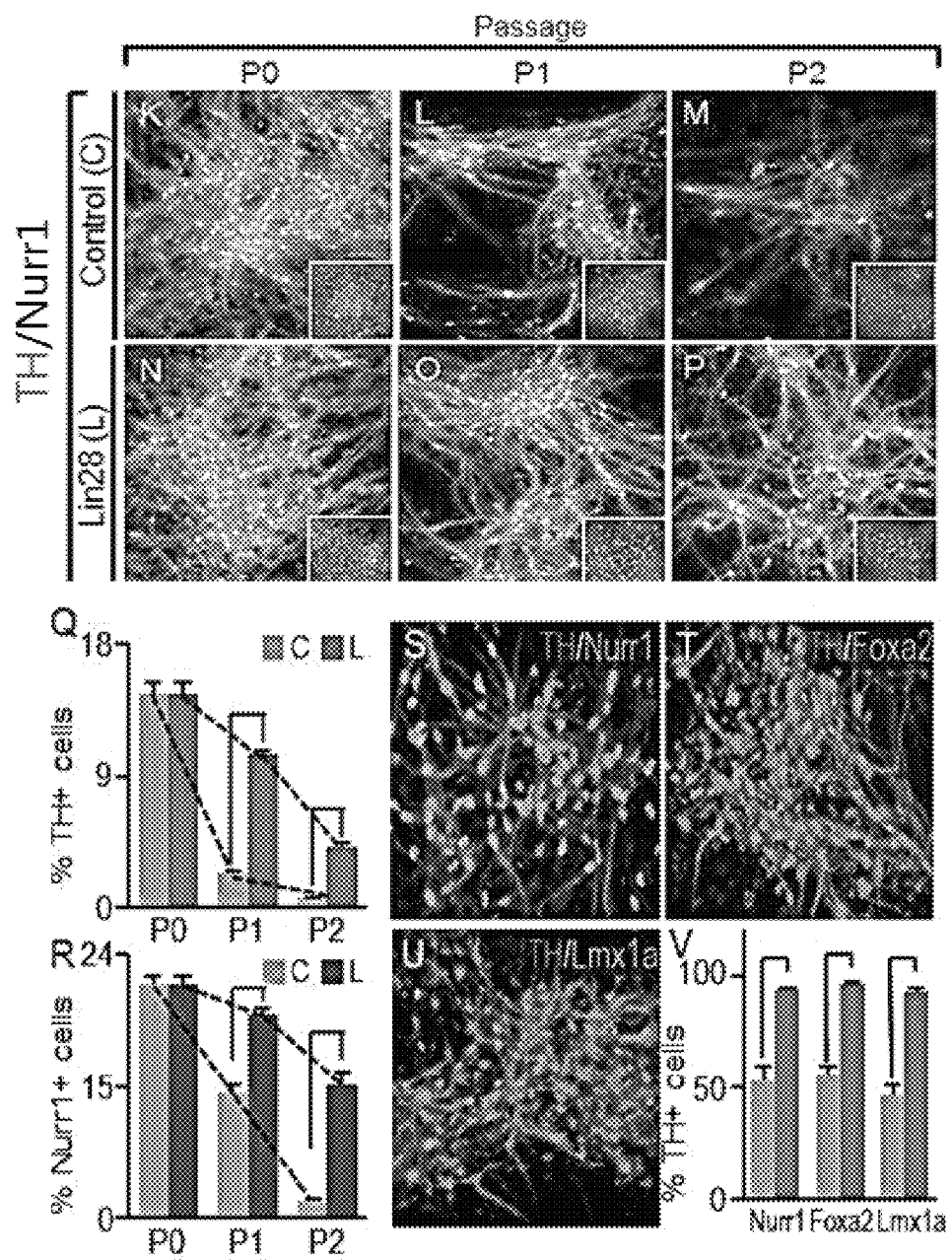

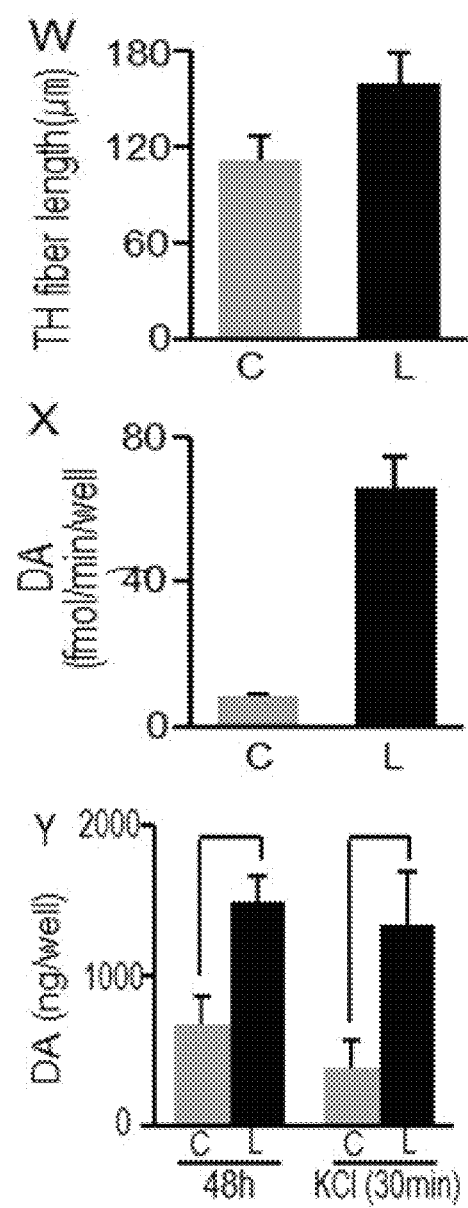
[FIG. 3C]

[FIG. 4A]
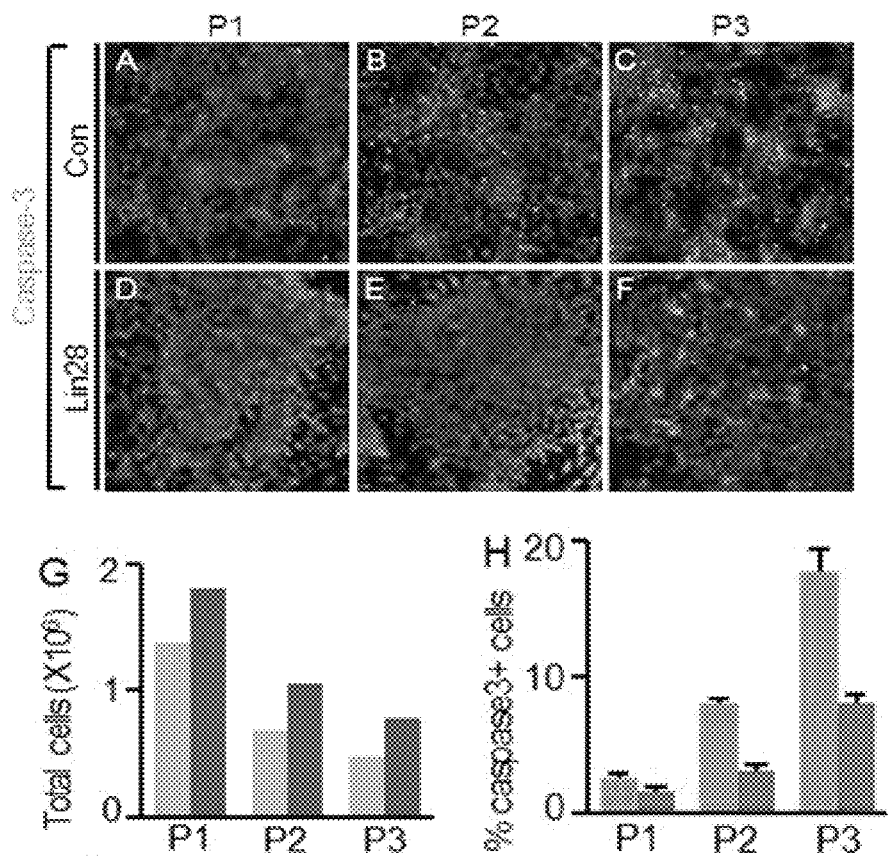

[FIG. 4B]
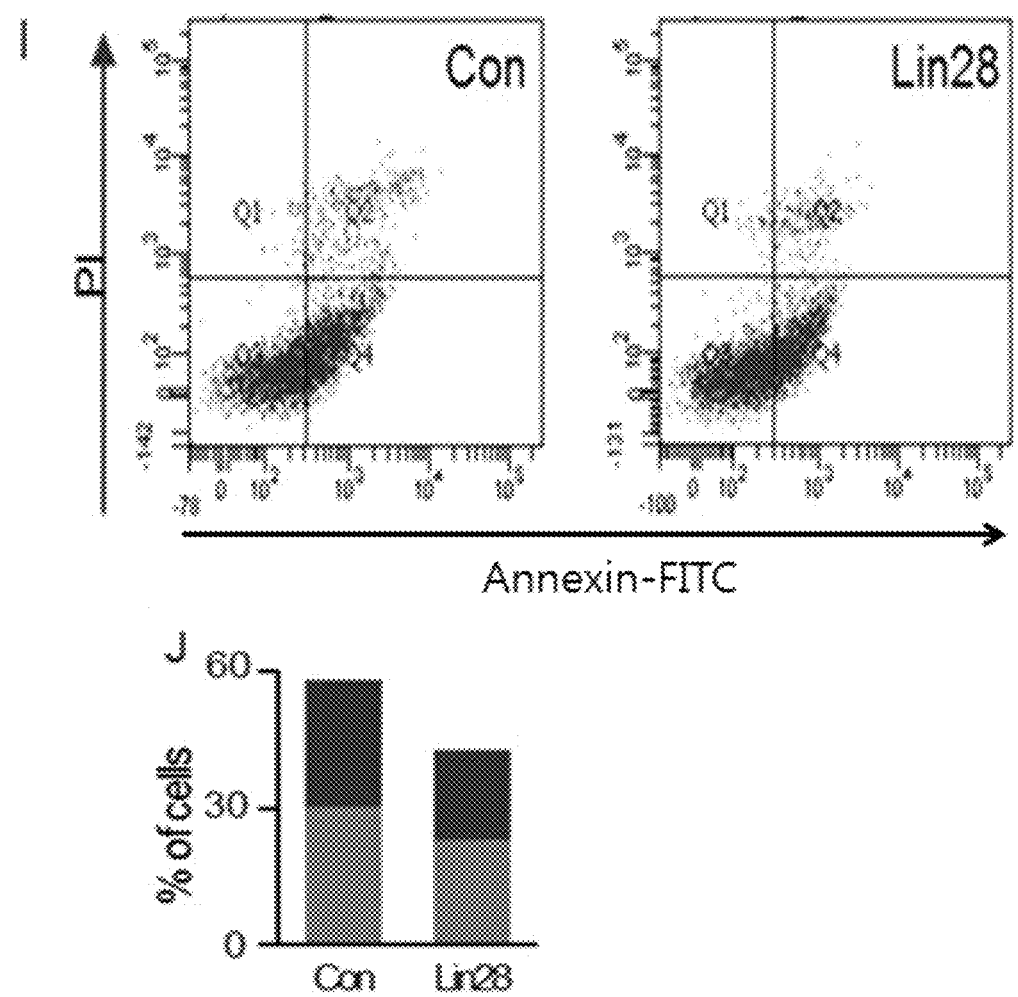

[FIG. 4C]
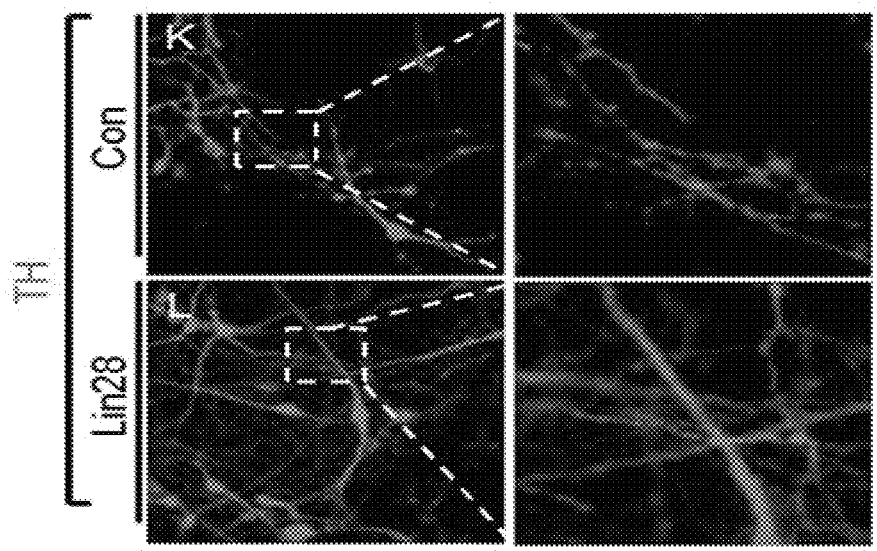
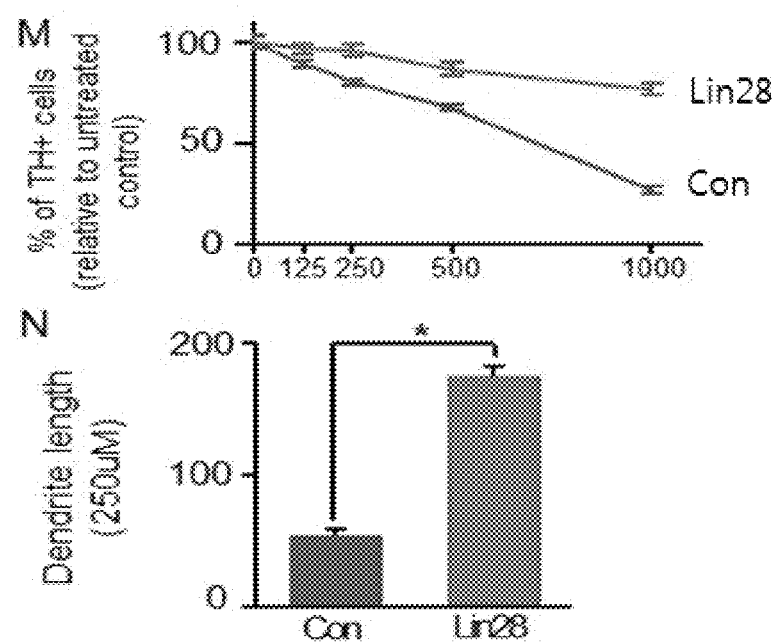

[FIG. 5A]
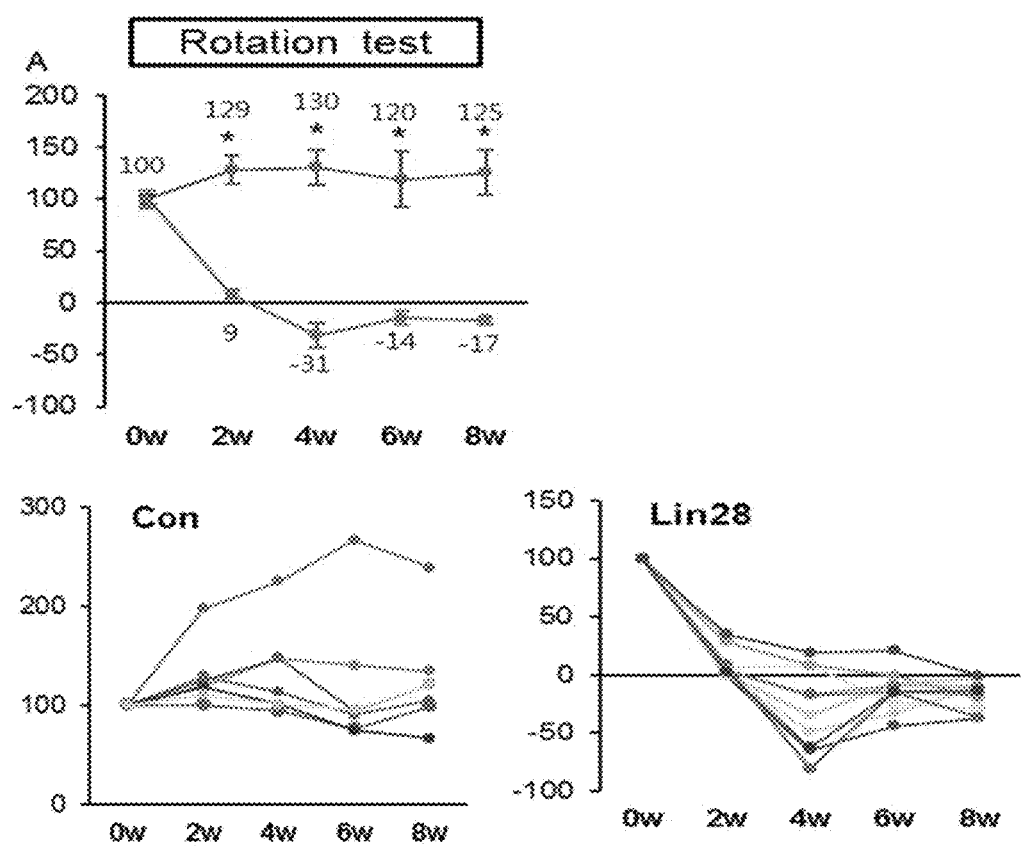

[FIG. 5B]
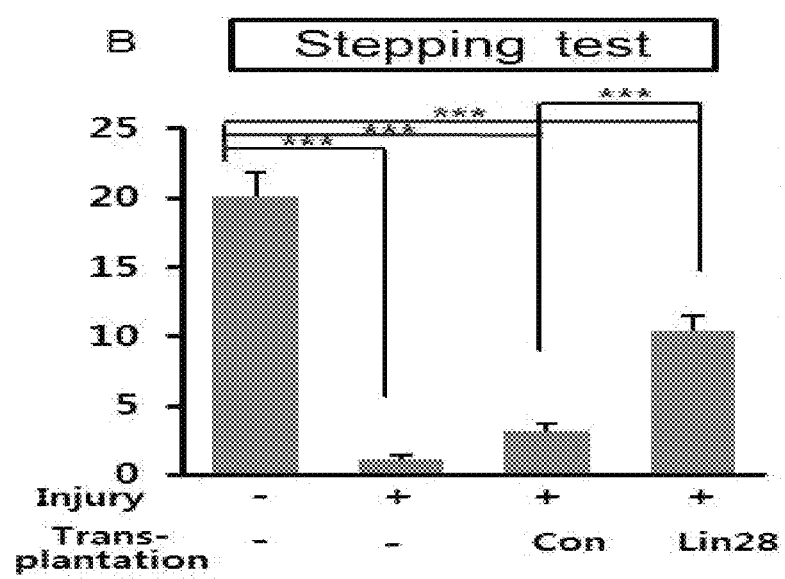

[FIG. 5C]
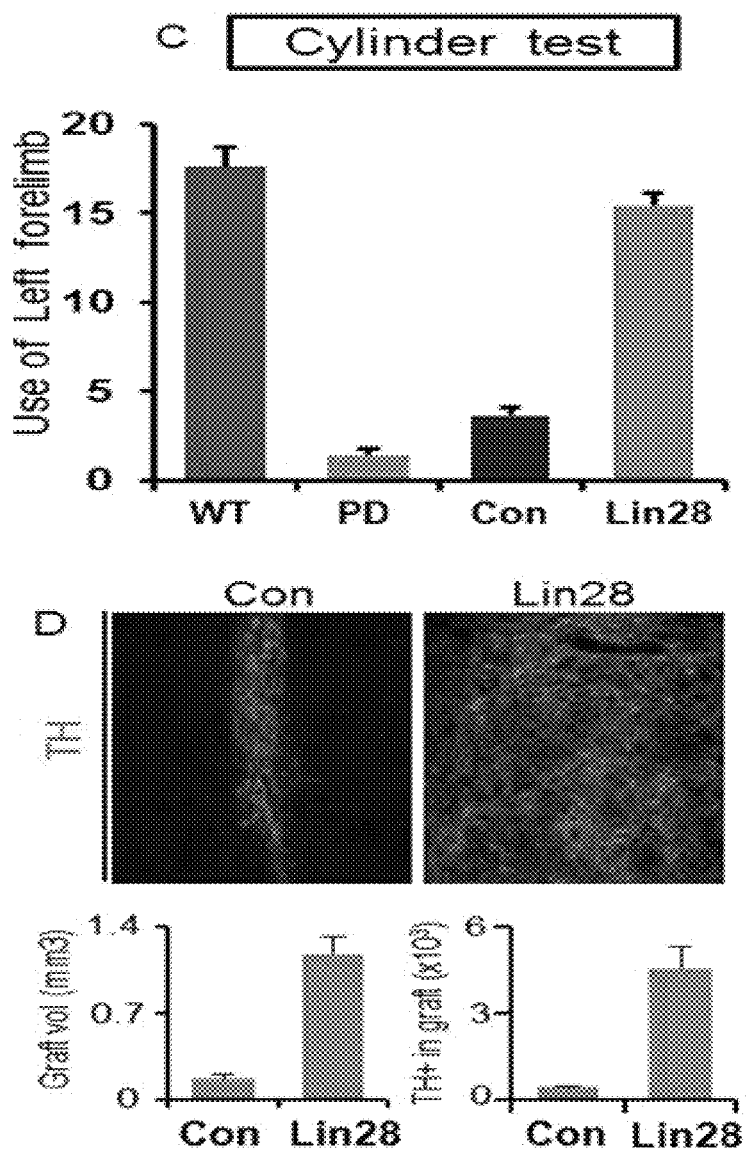

[FIG. 5D]
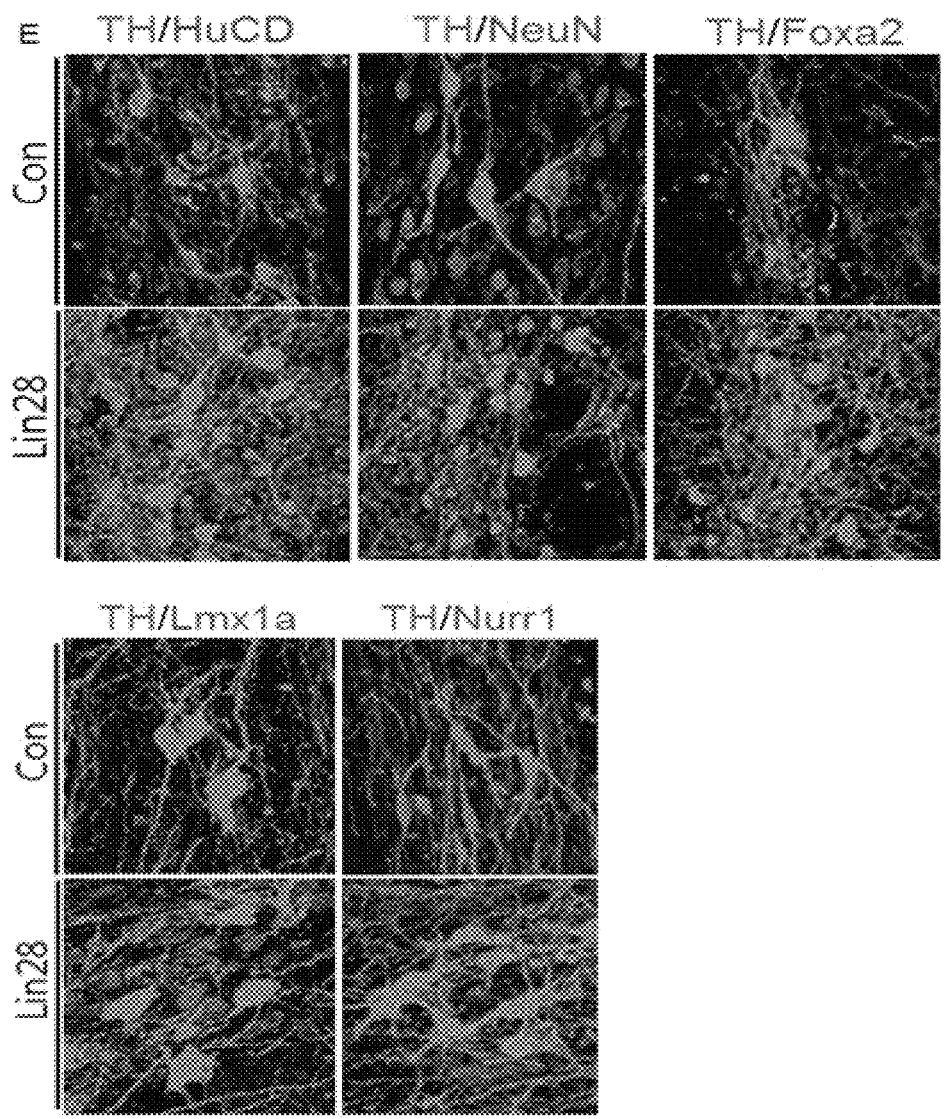

[FIG. 6A]
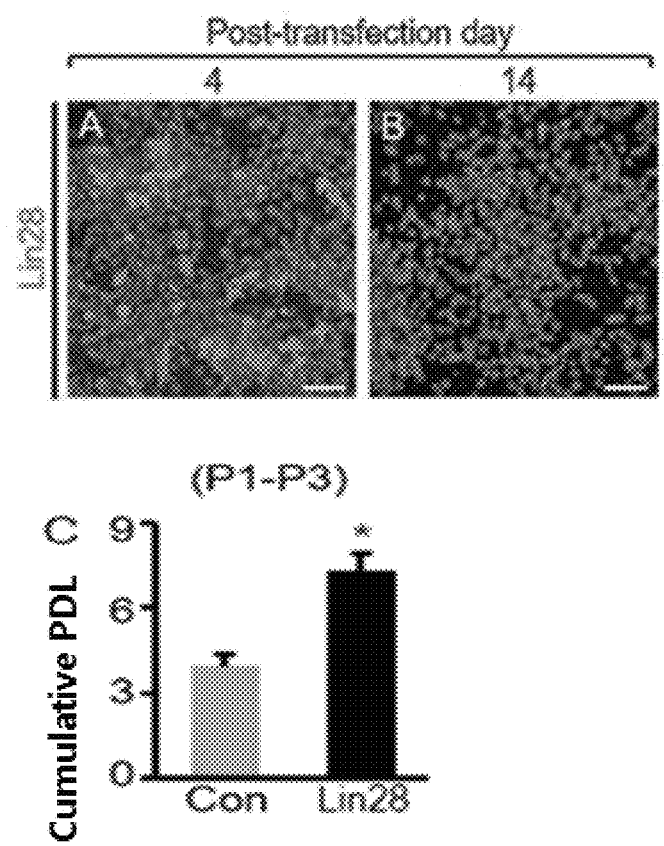

[FIG. 6B]
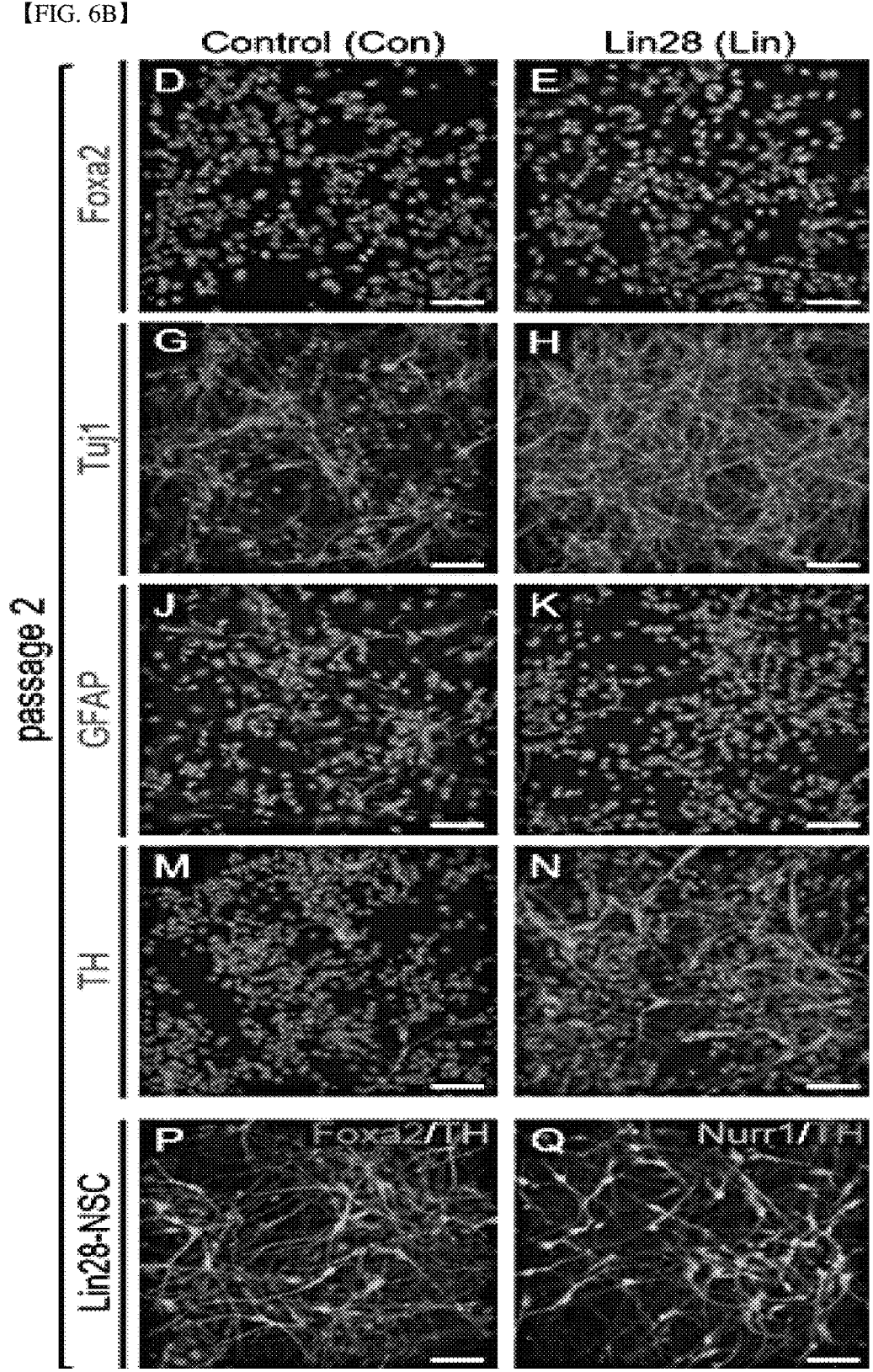

[FIG. 6C]
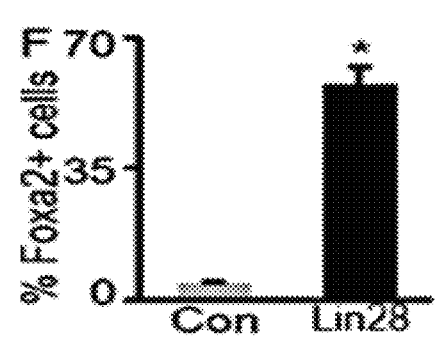
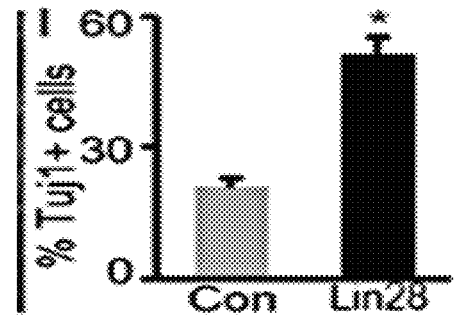
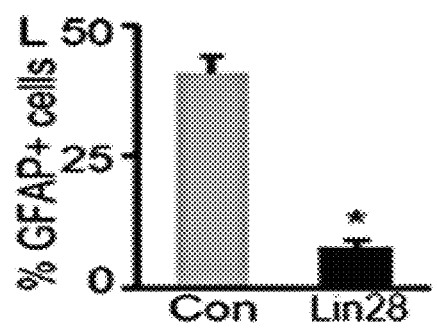
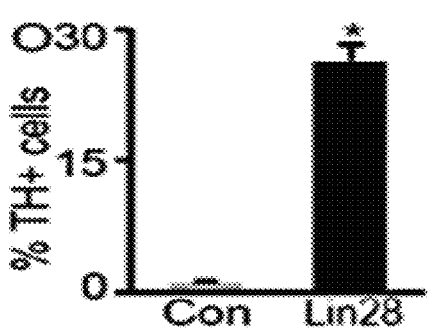
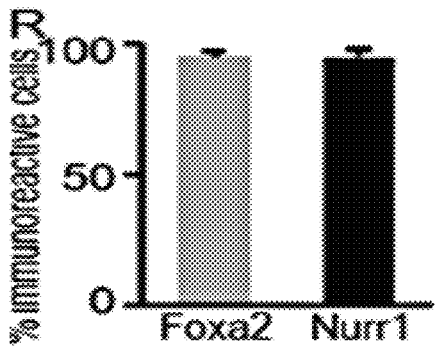

[FIG. 7A]
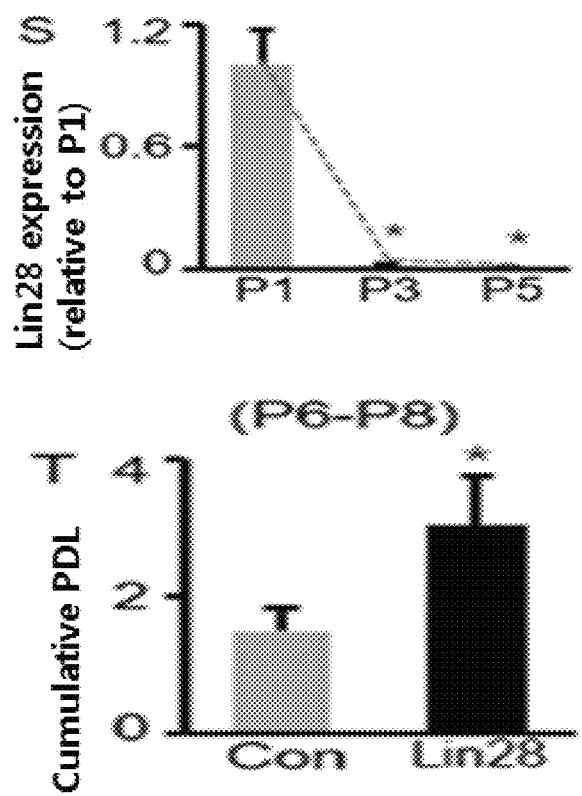

[FIG. 7B]
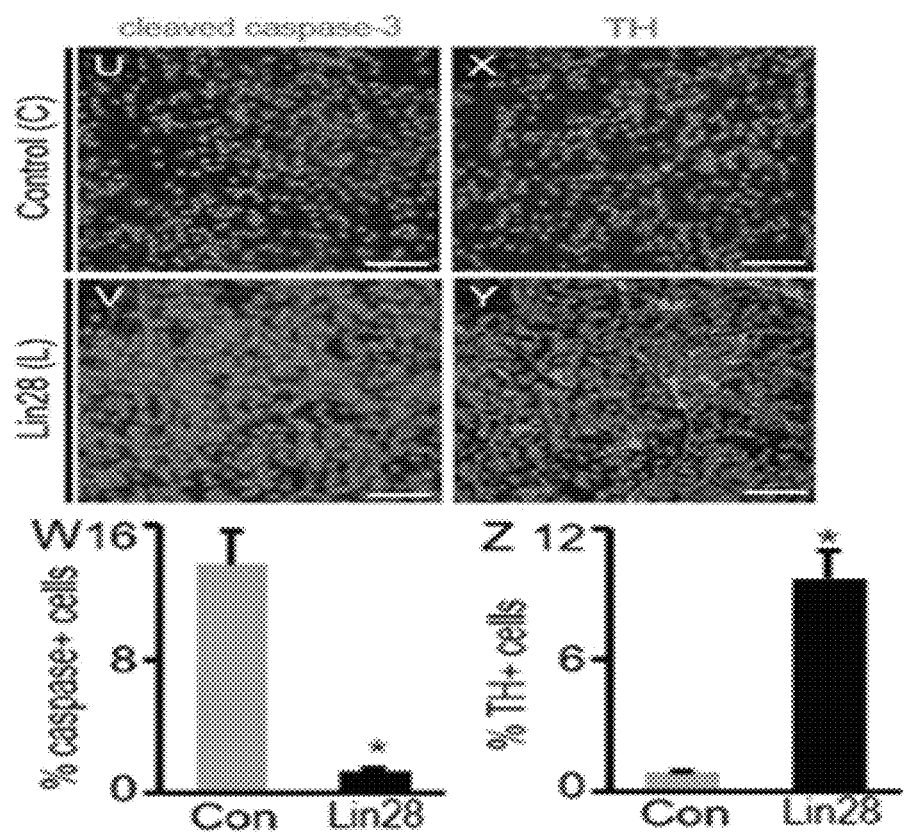

[FIG. 8]
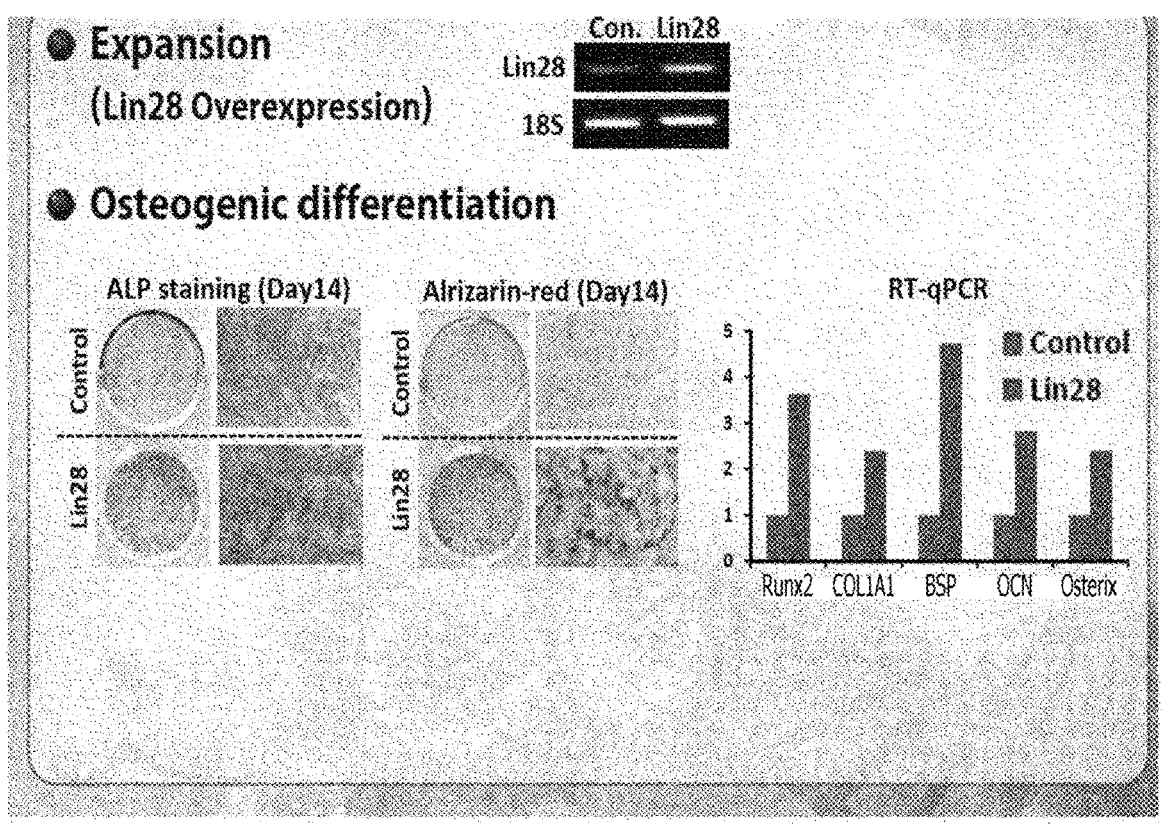

[FIG. 9]
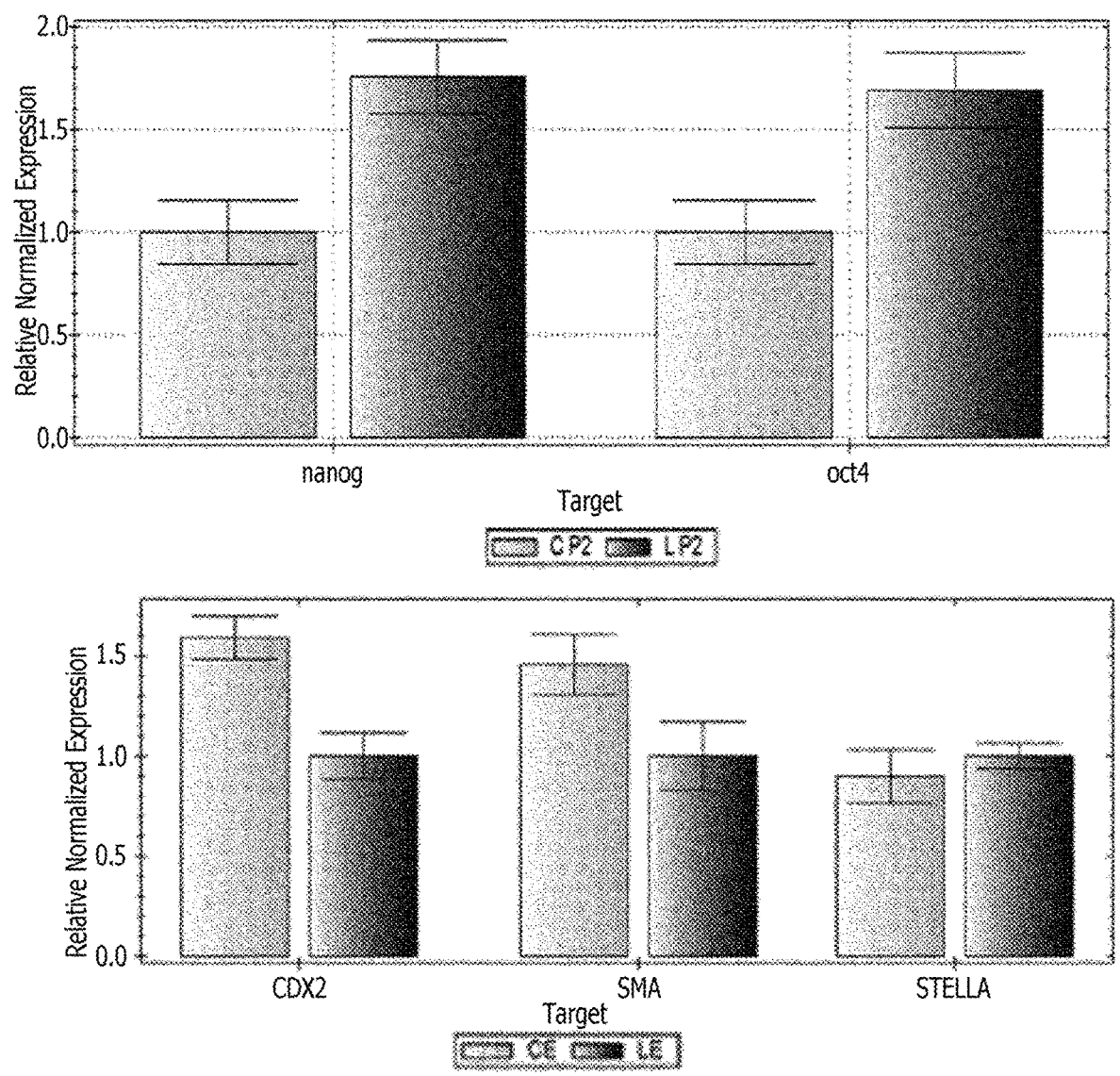

[FIG. 10]
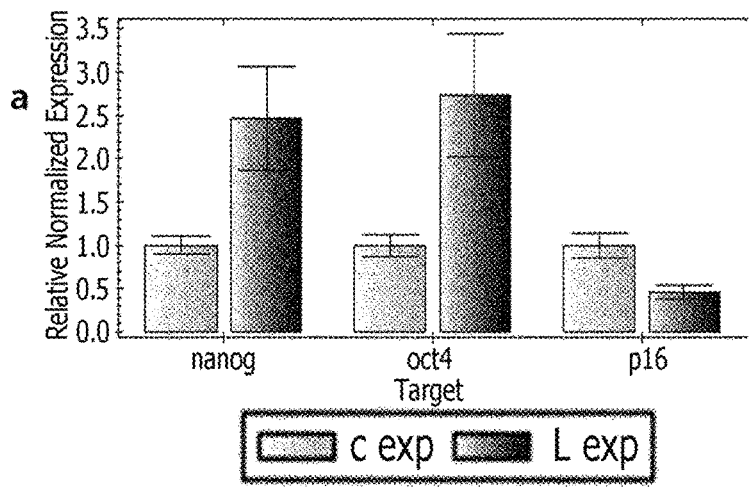
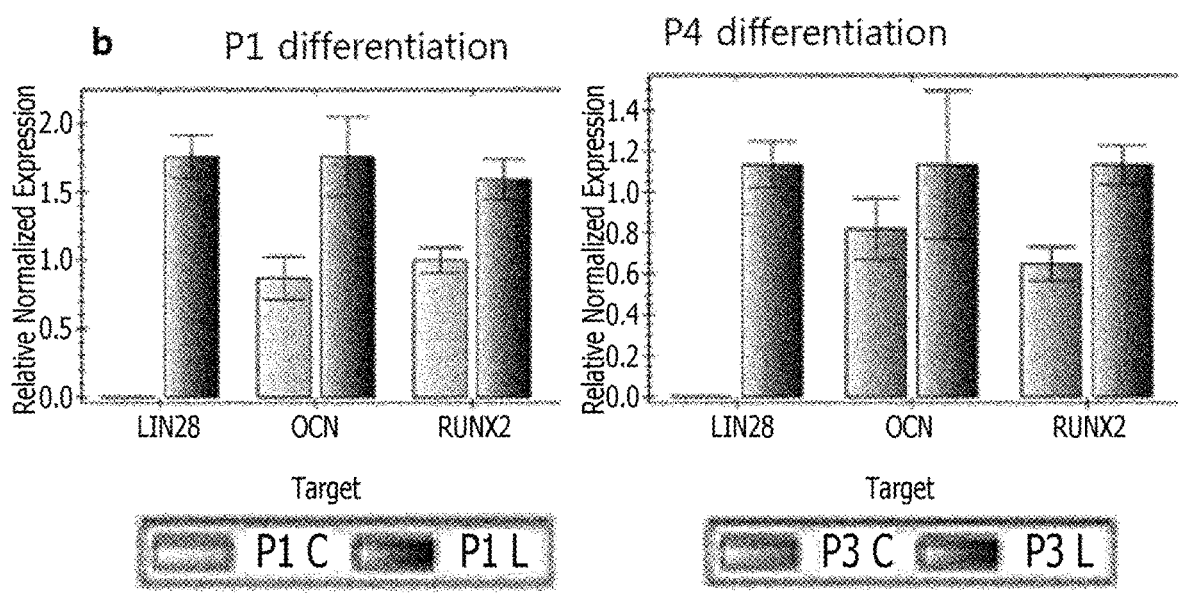

[FIG. 11]
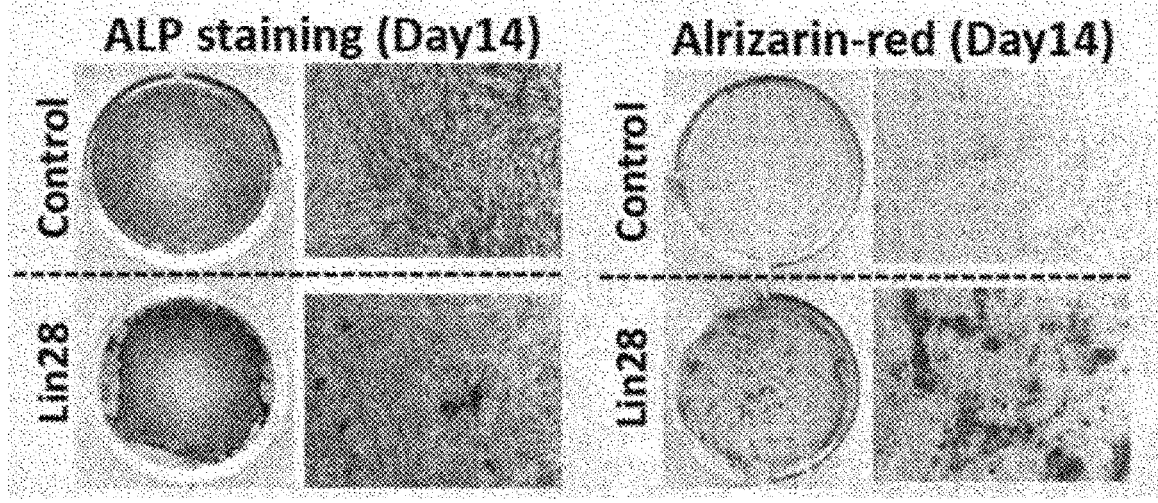
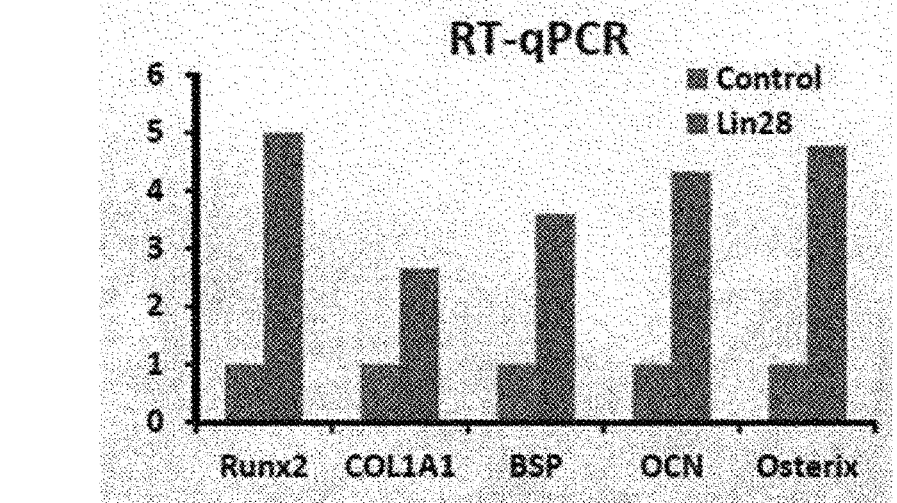

[FIG. 12]
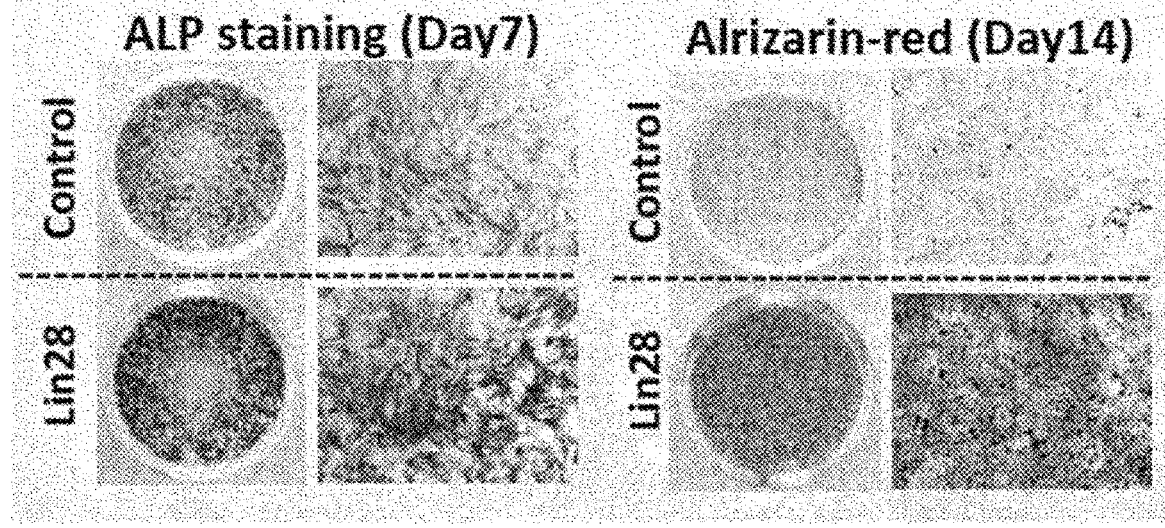
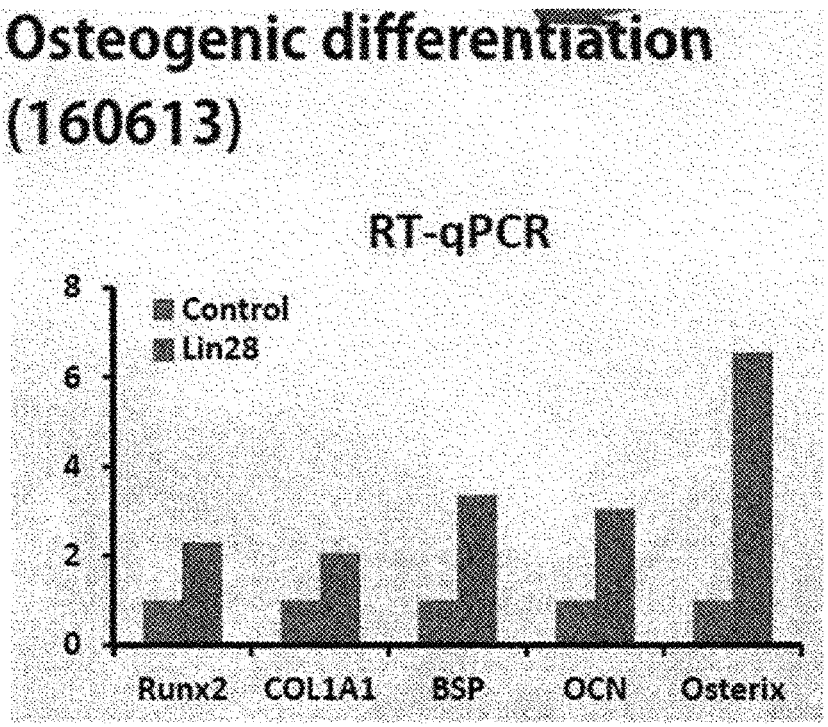

[FIG. 13]
● chondrogenic differentiation
Safranin-O staining (Day21)
GFP　　　　　Lin28　　　　Control (TGFβ-
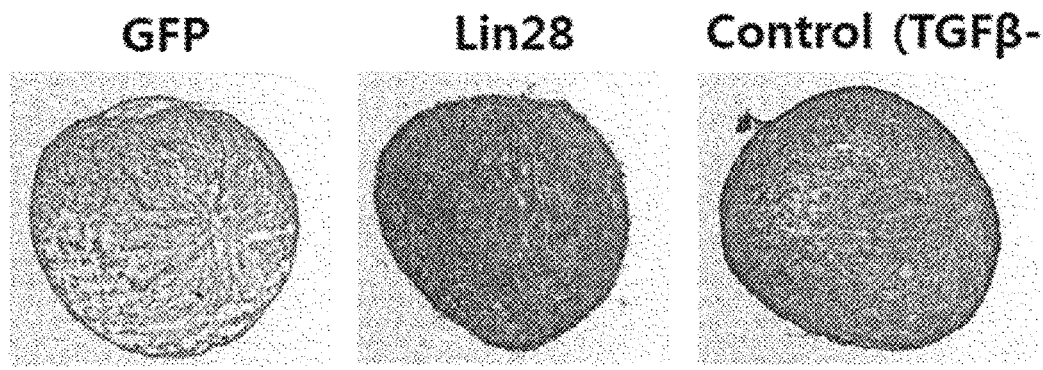
RT-qPCR
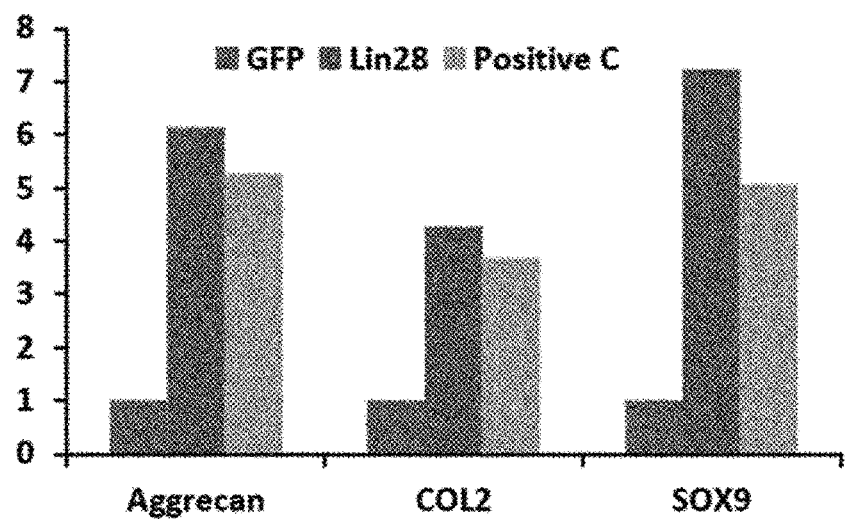

[FIG. 14]
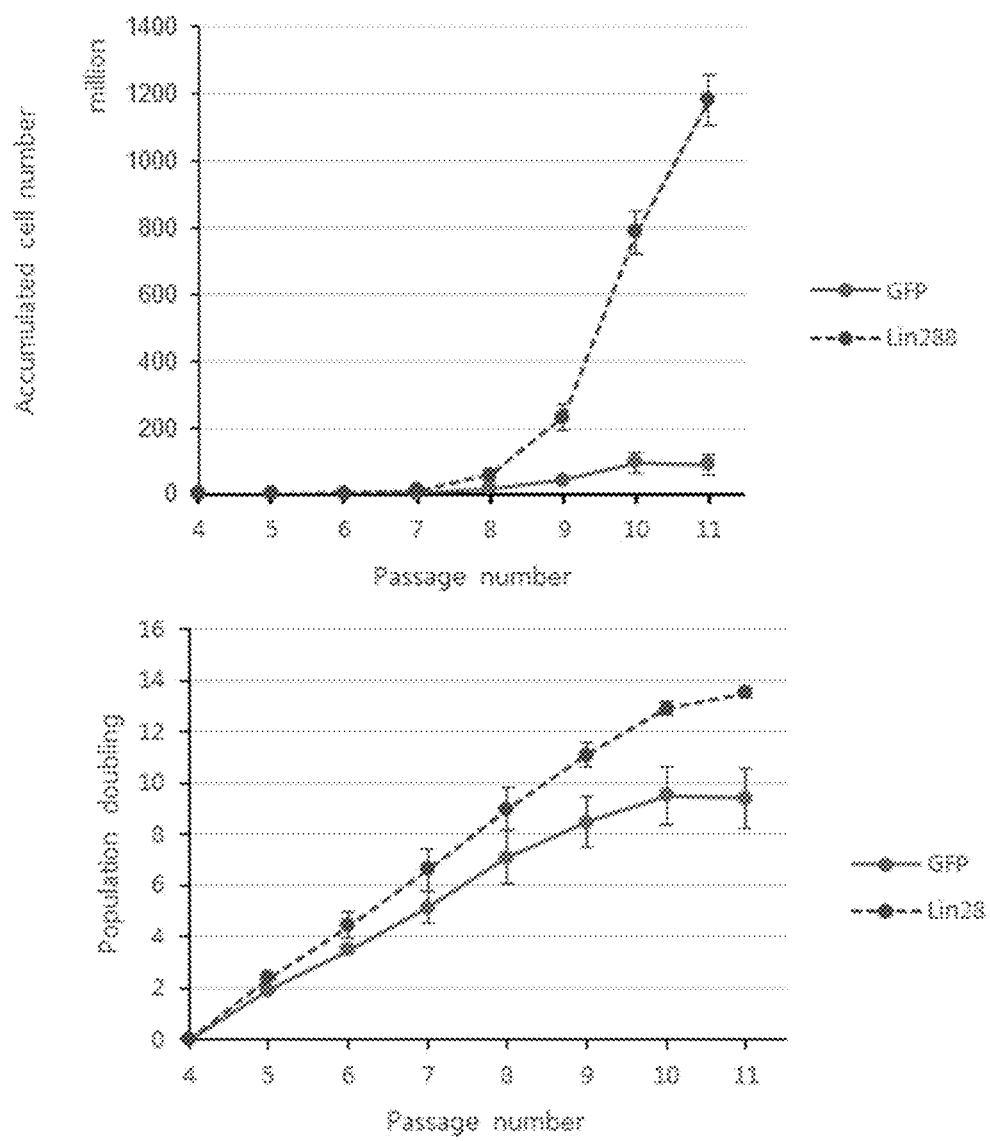

[FIG. 15A]
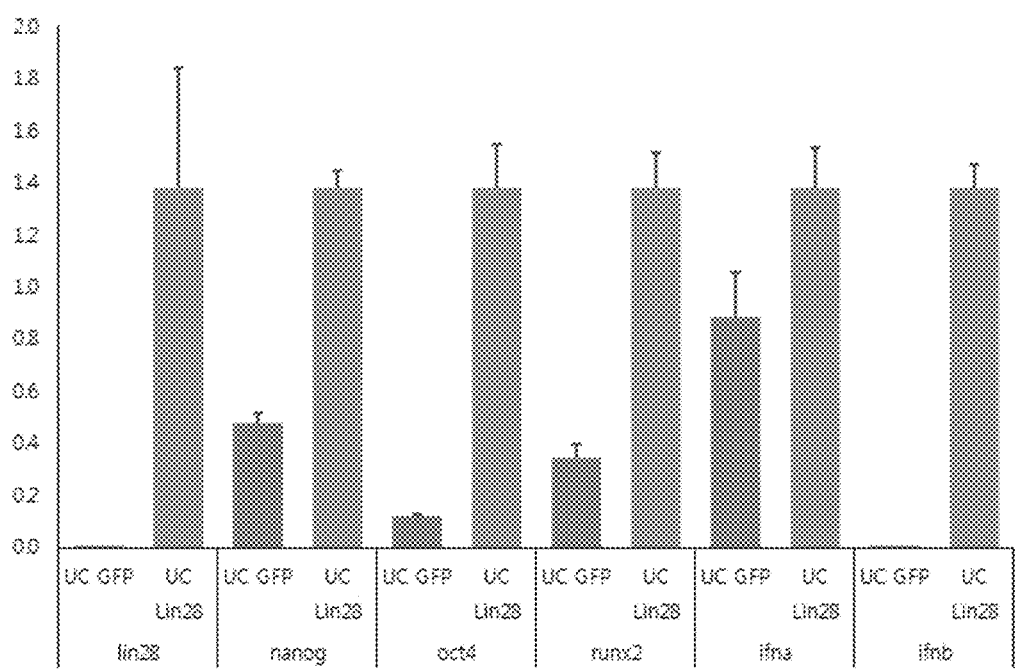

【FIG. 15B】
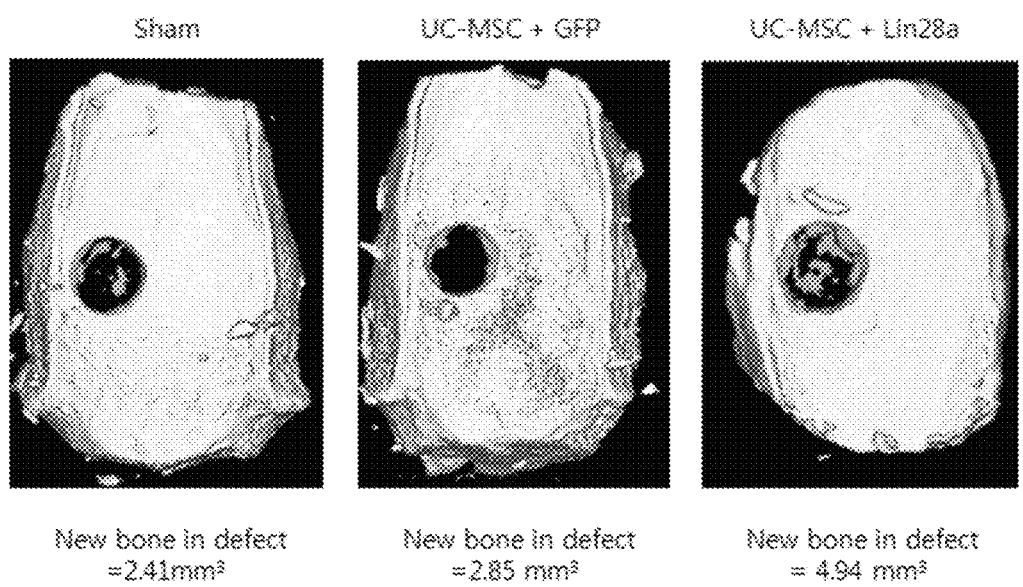

[FIG. 16A]
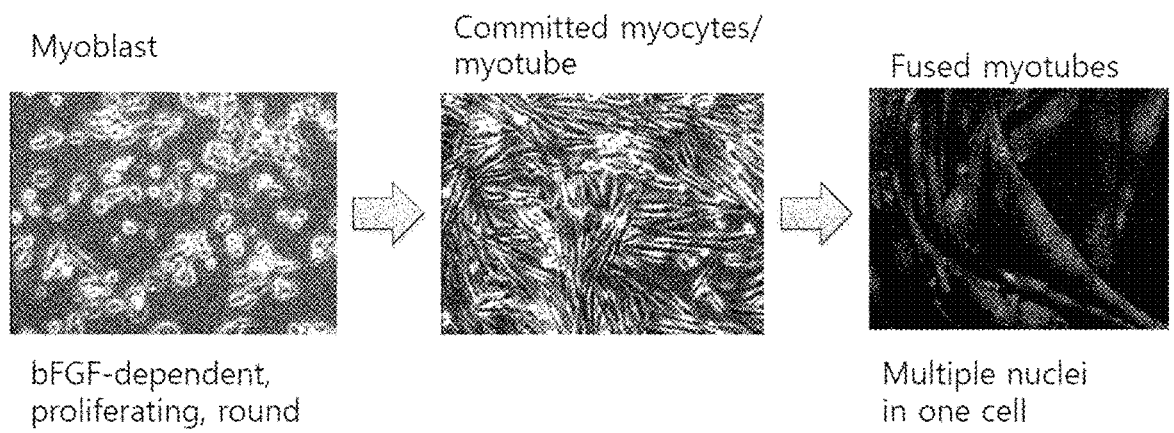

[FIG. 16B]
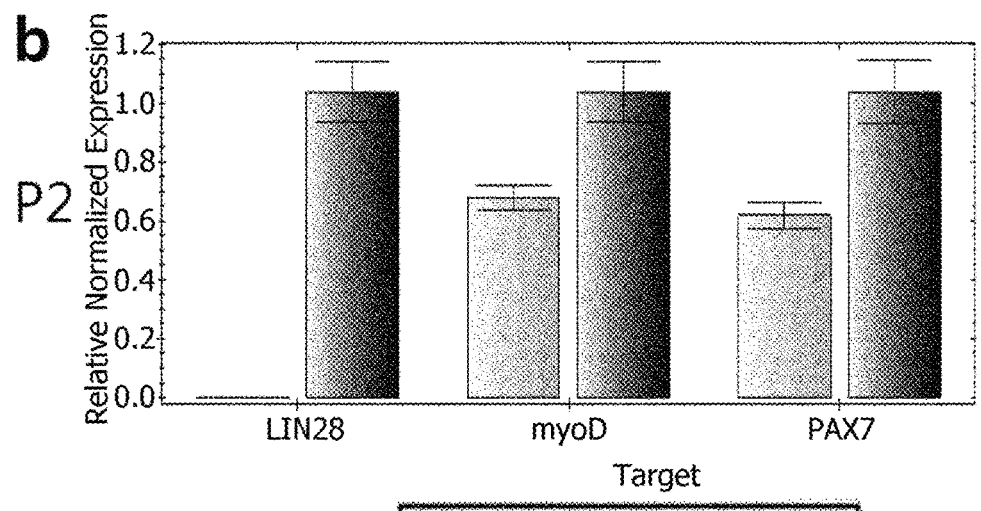
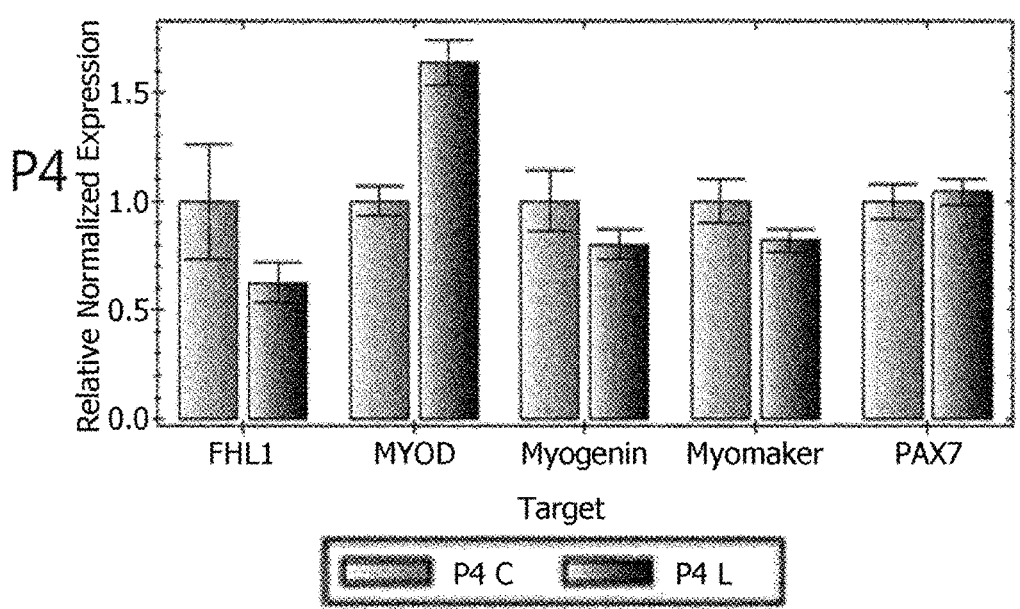

[FIG. 16C]
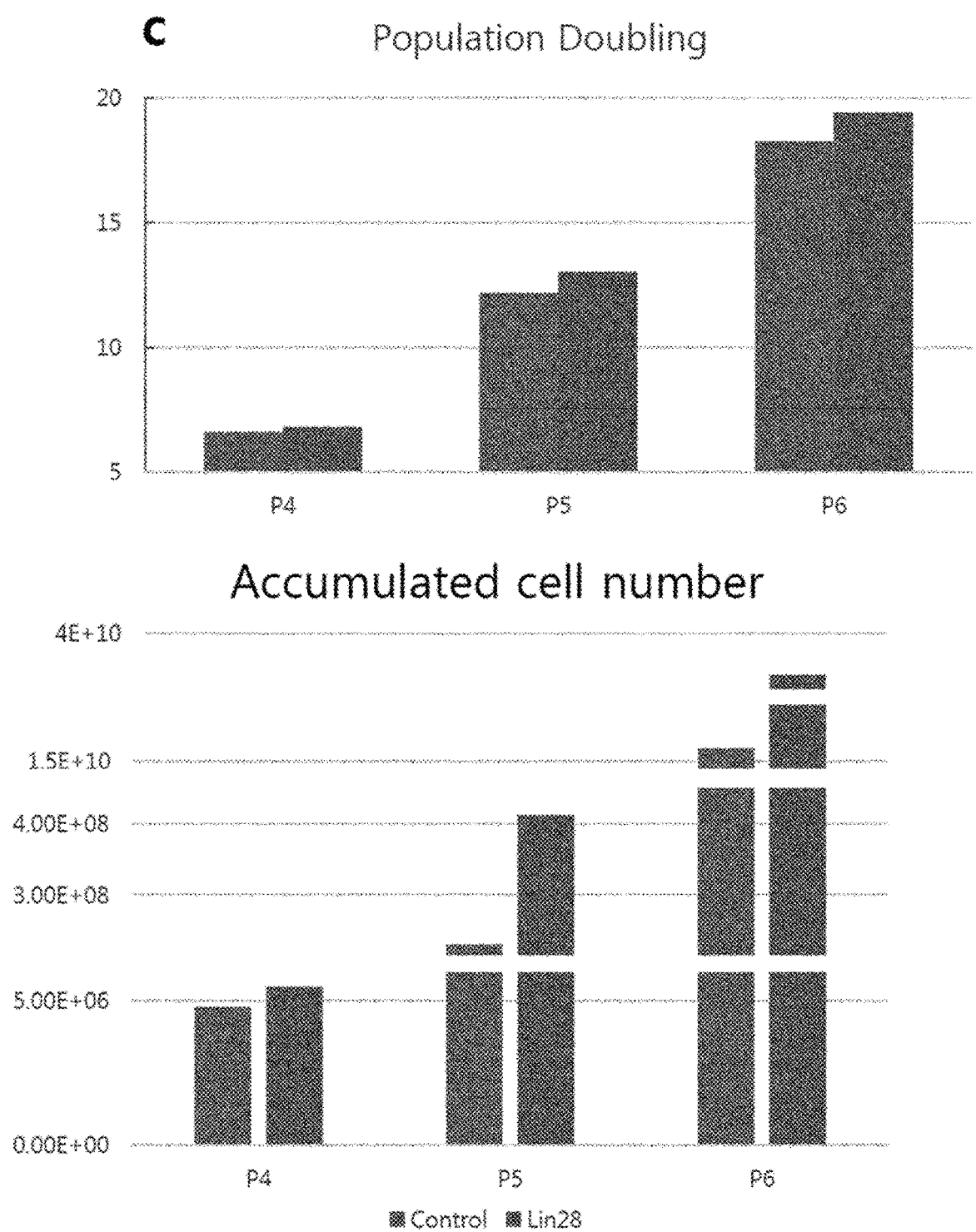

[FIG. 17]
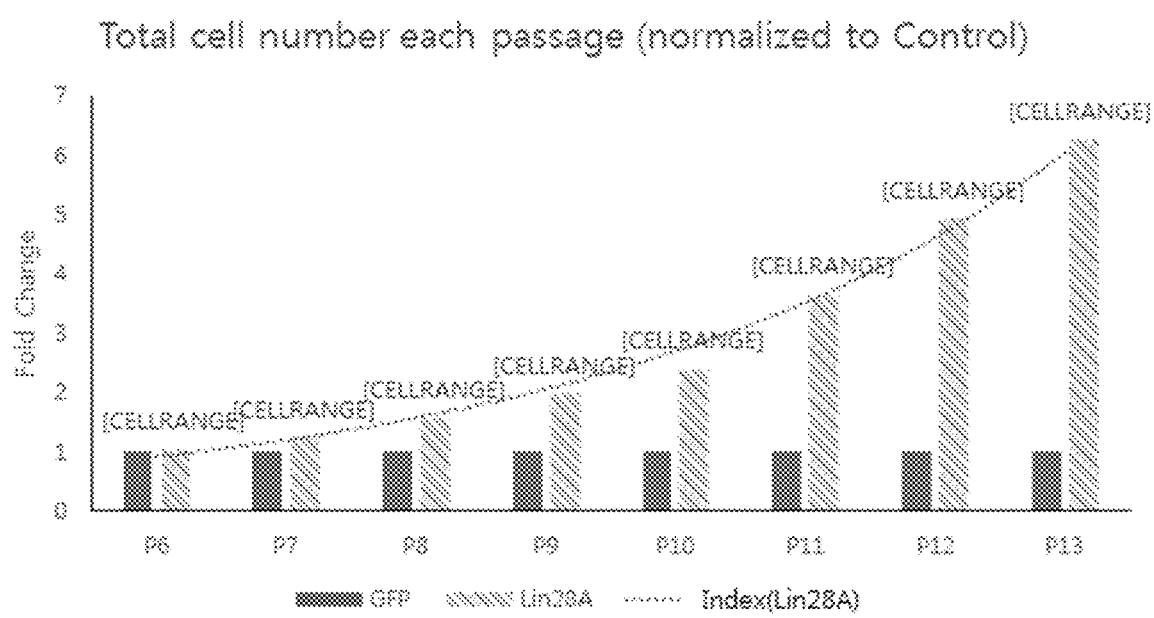

[FIG. 18A]
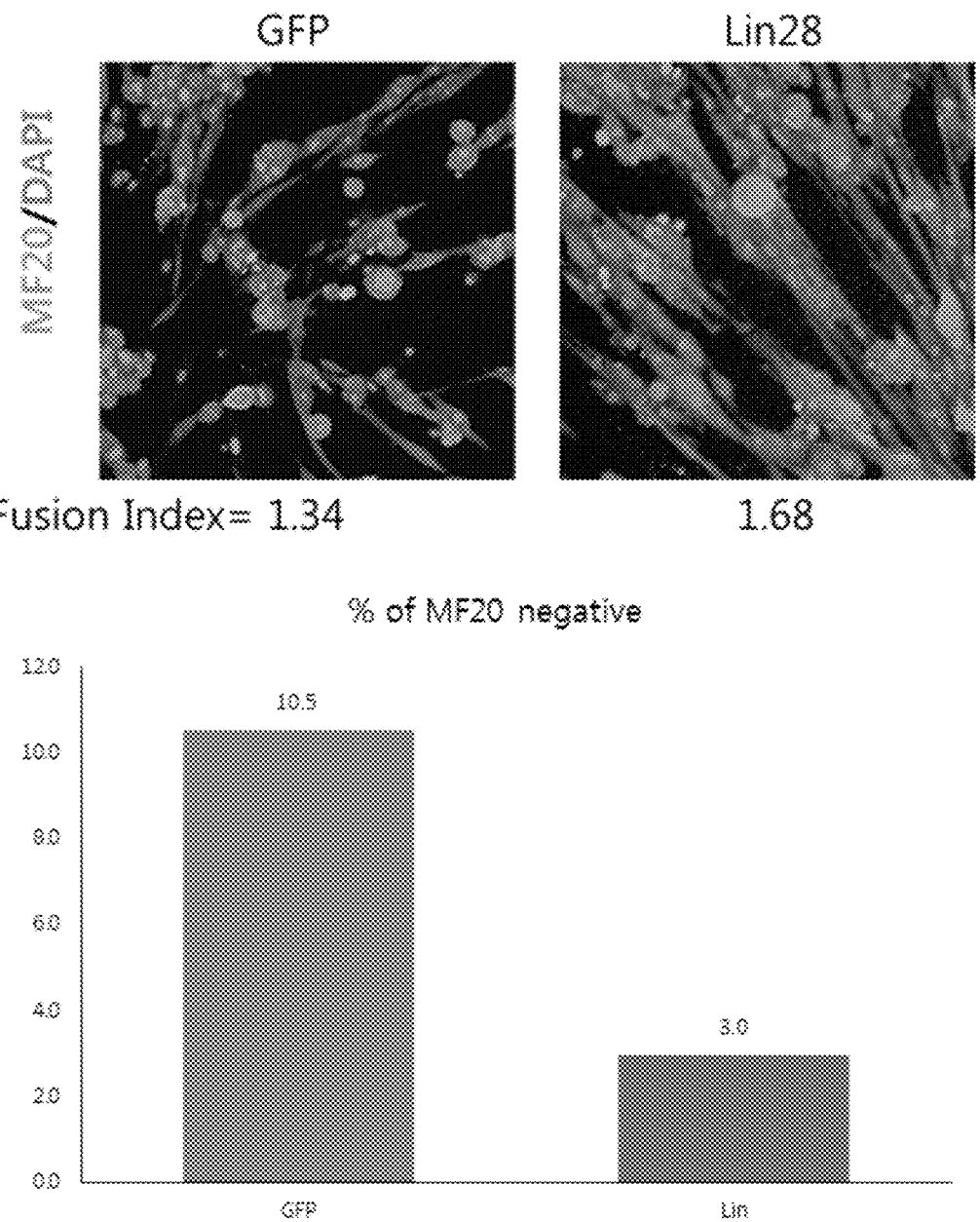

[FIG. 18B]
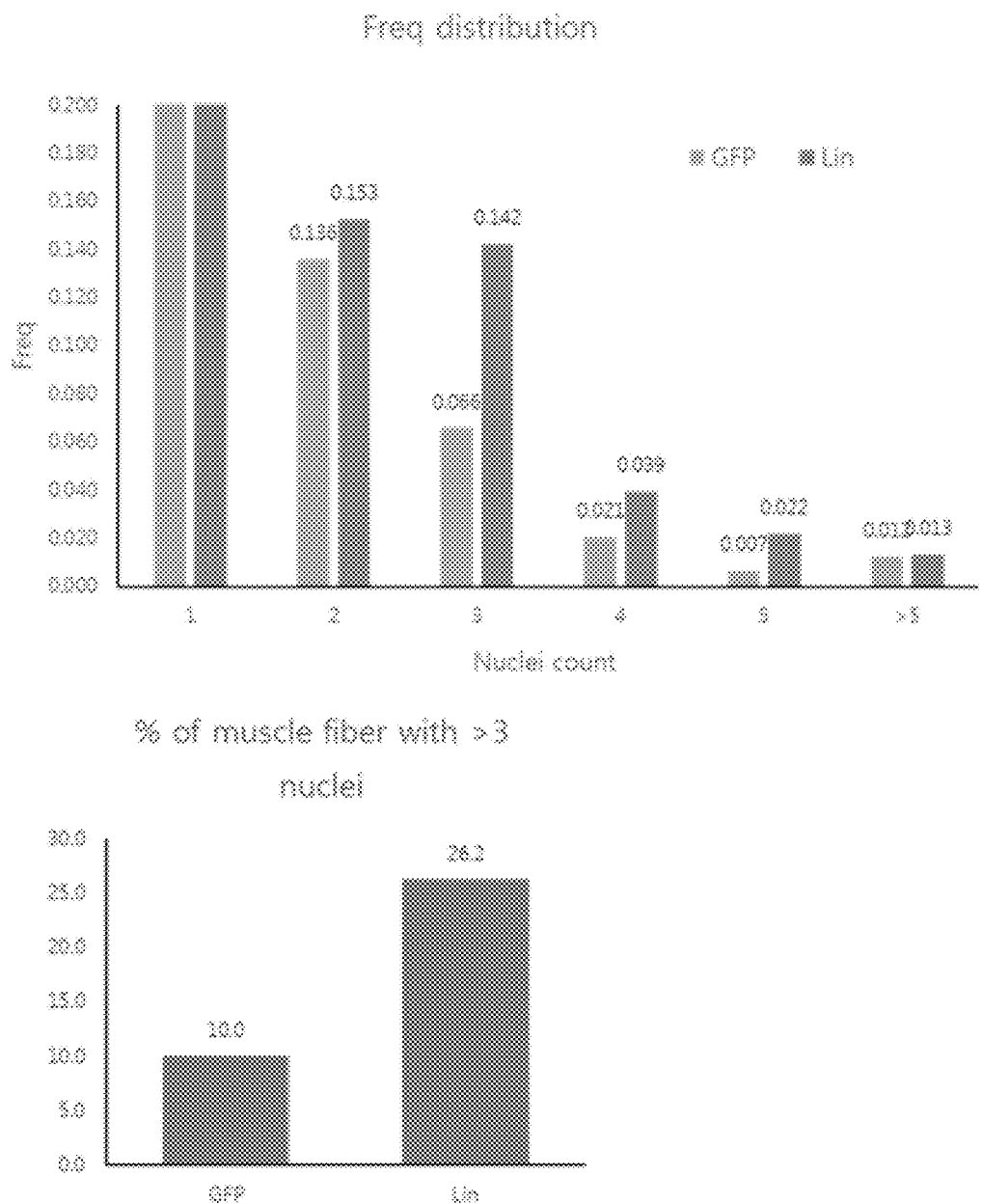

[FIG. 19A]
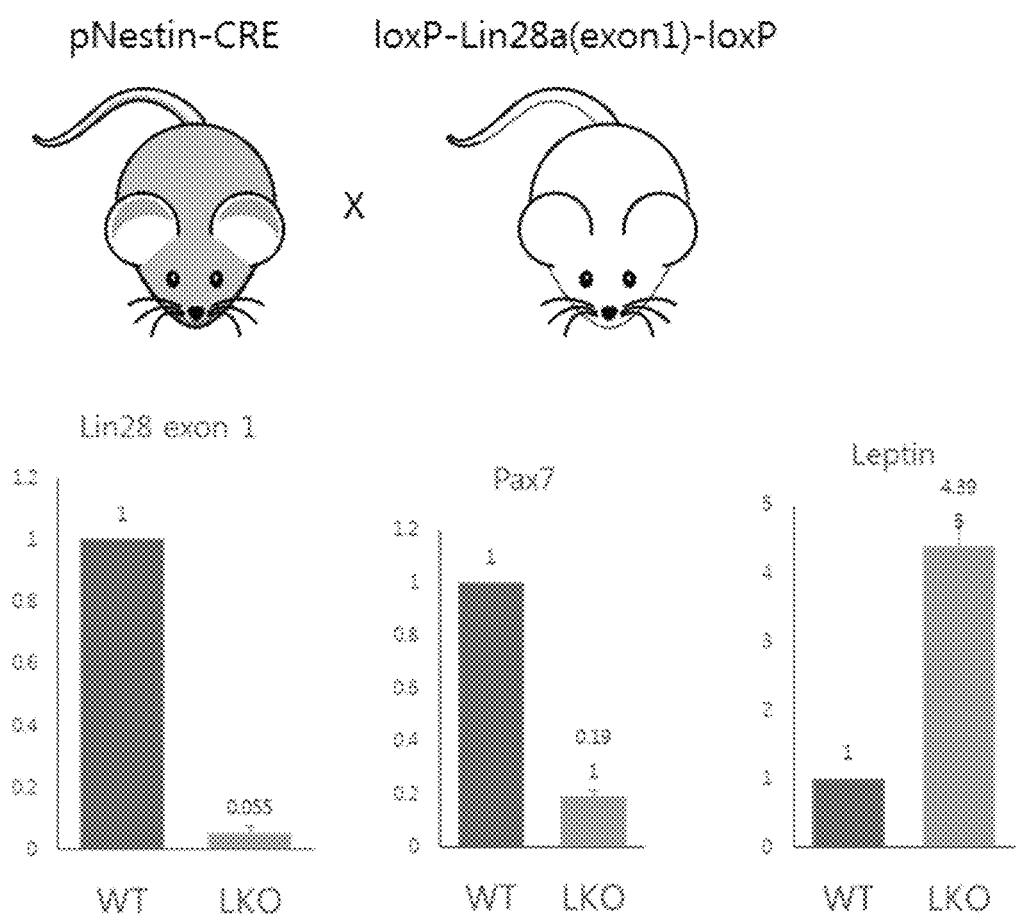

[FIG. 19B]
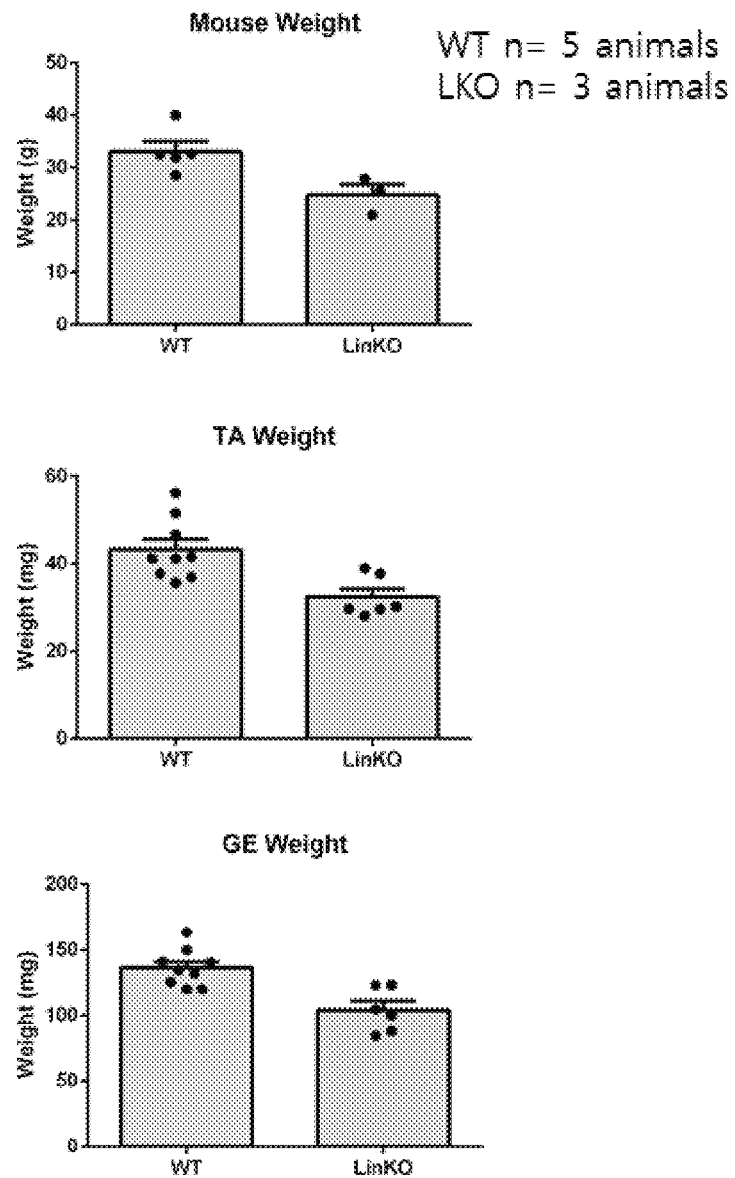

[FIG. 20]
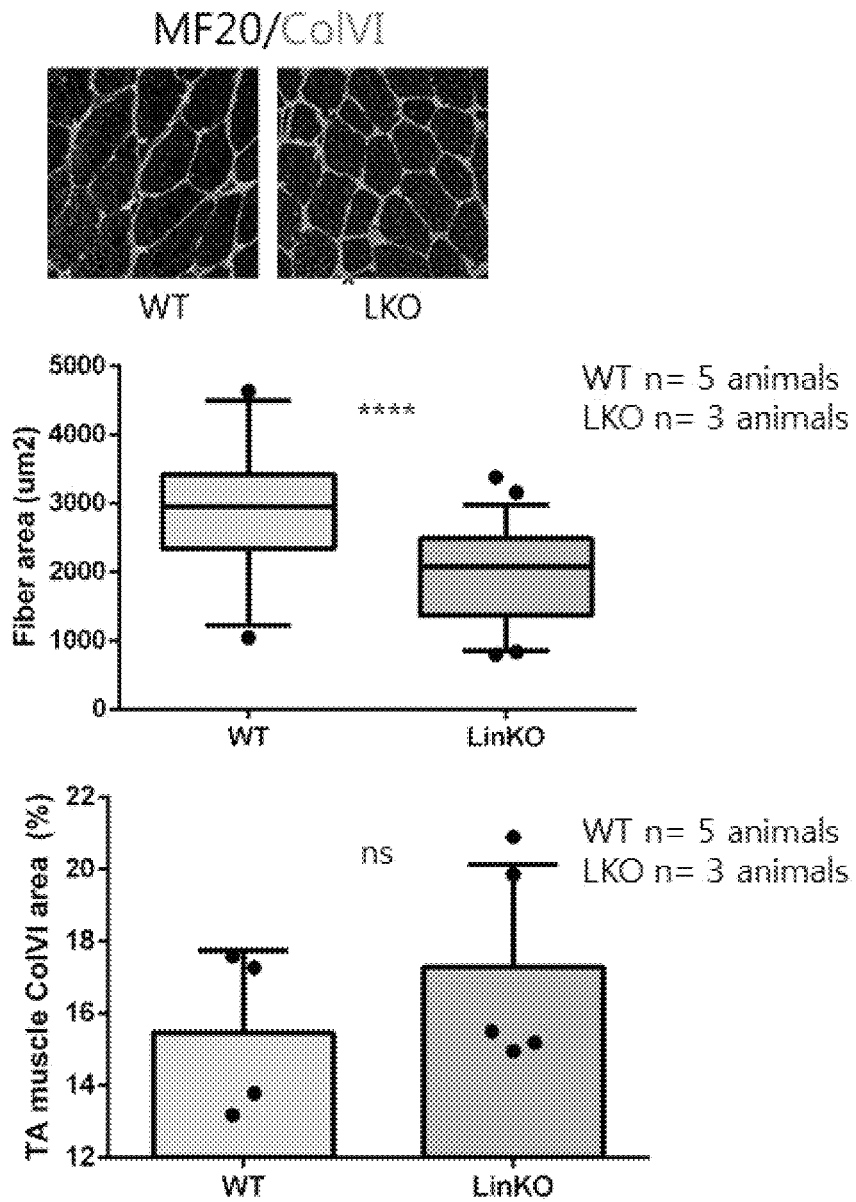

[FIG. 21]
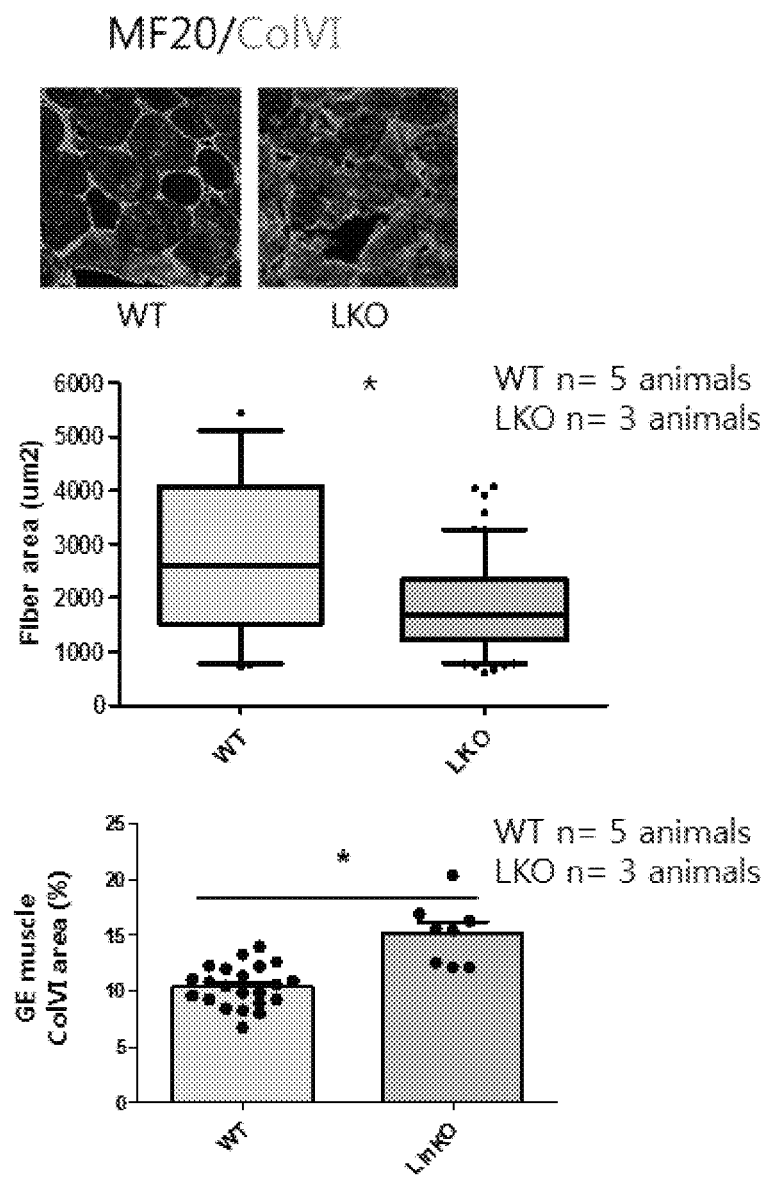

[FIG. 22A]
a
P7 Con  P7 Lin
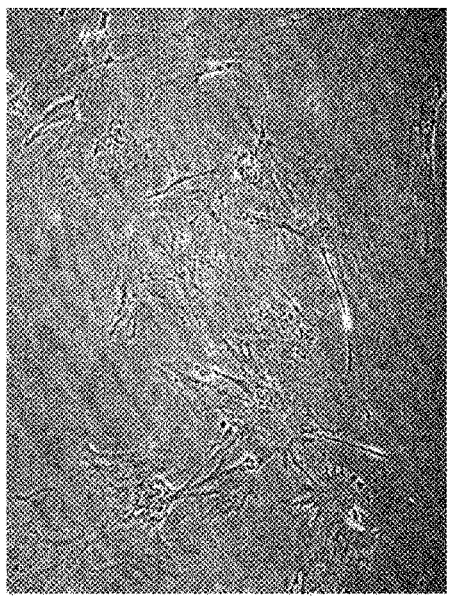 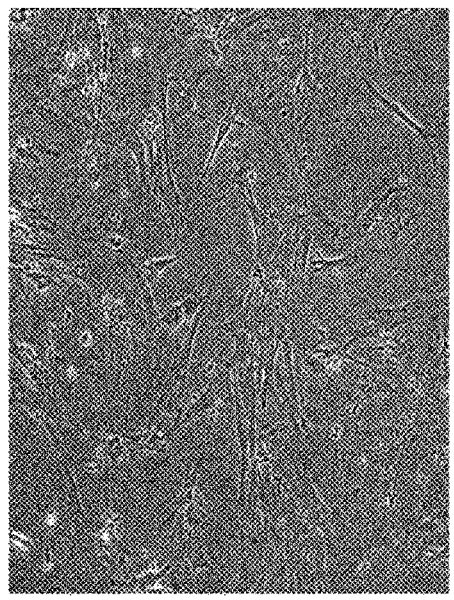
Total cell number
($\times 10^6$)
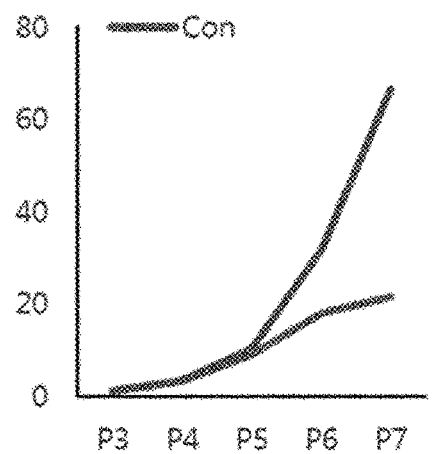

[FIG. 22B]
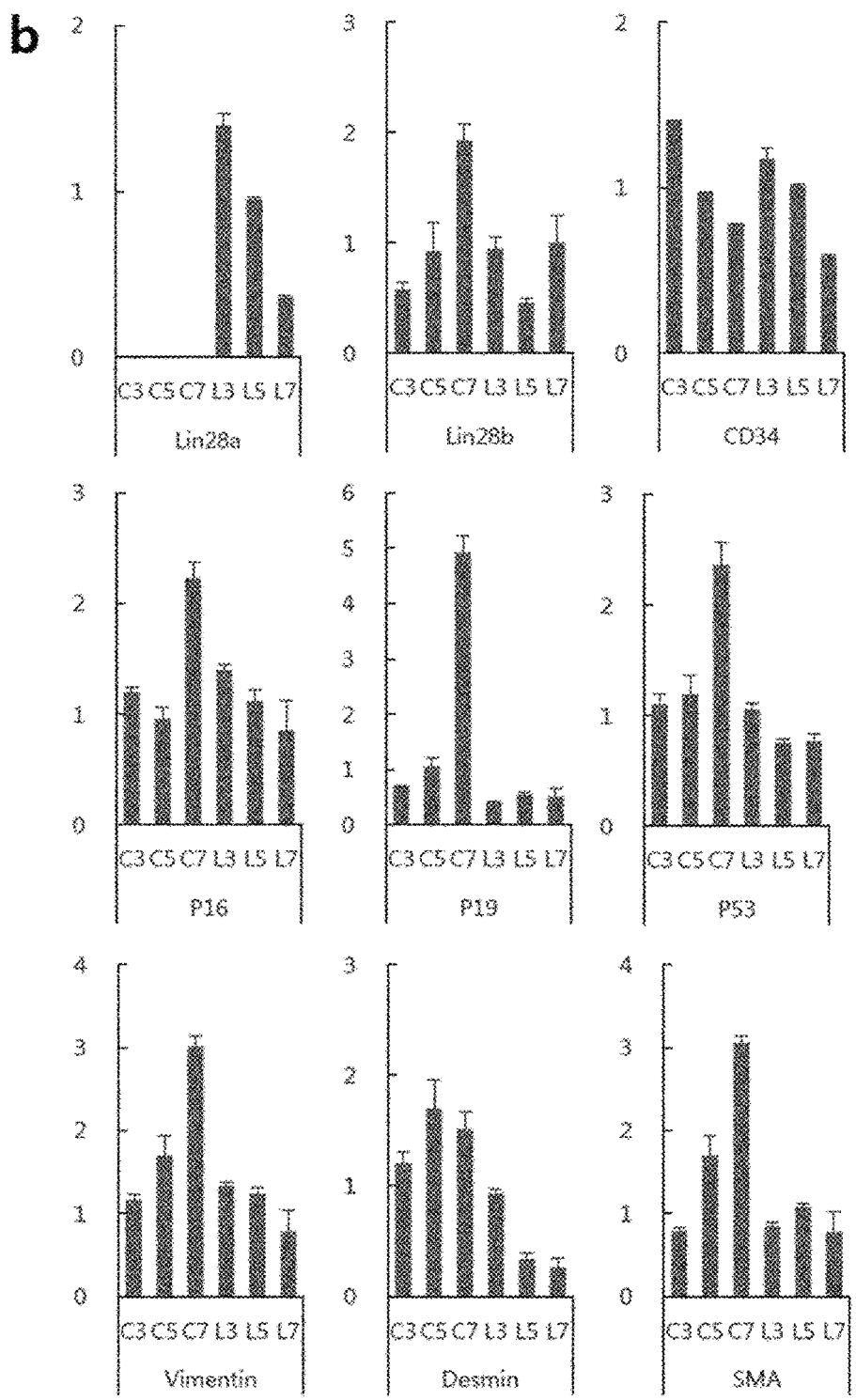

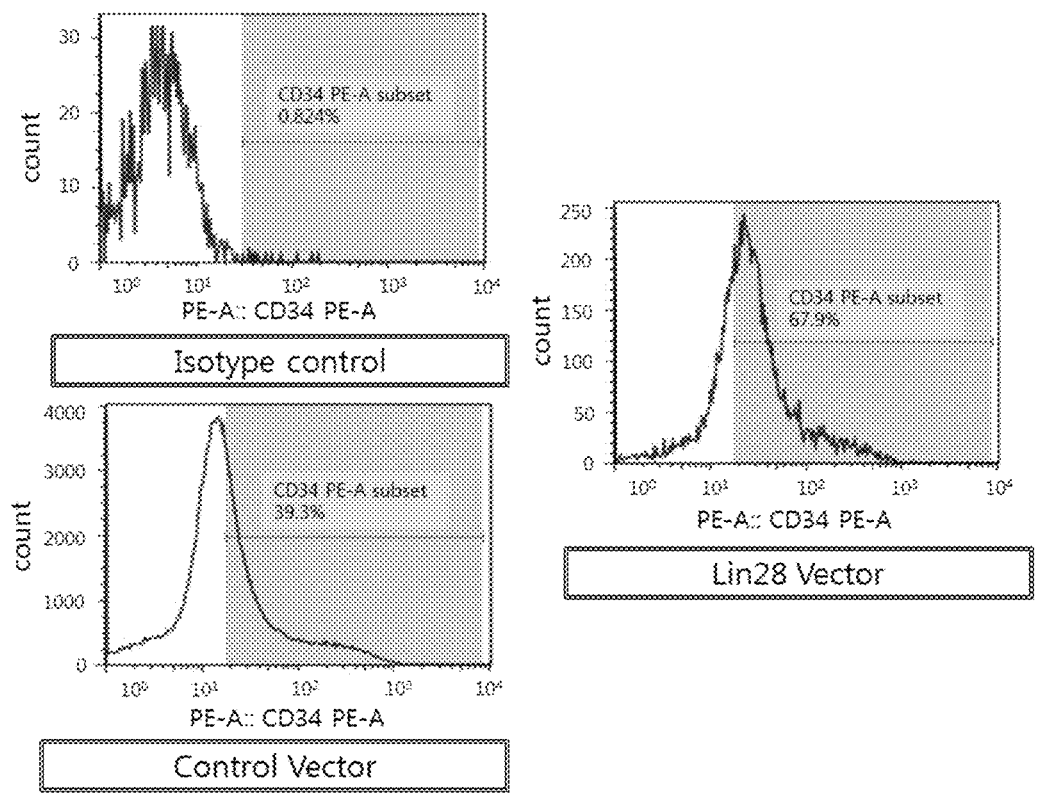
[FIG. 23]

[FIG. 24A]

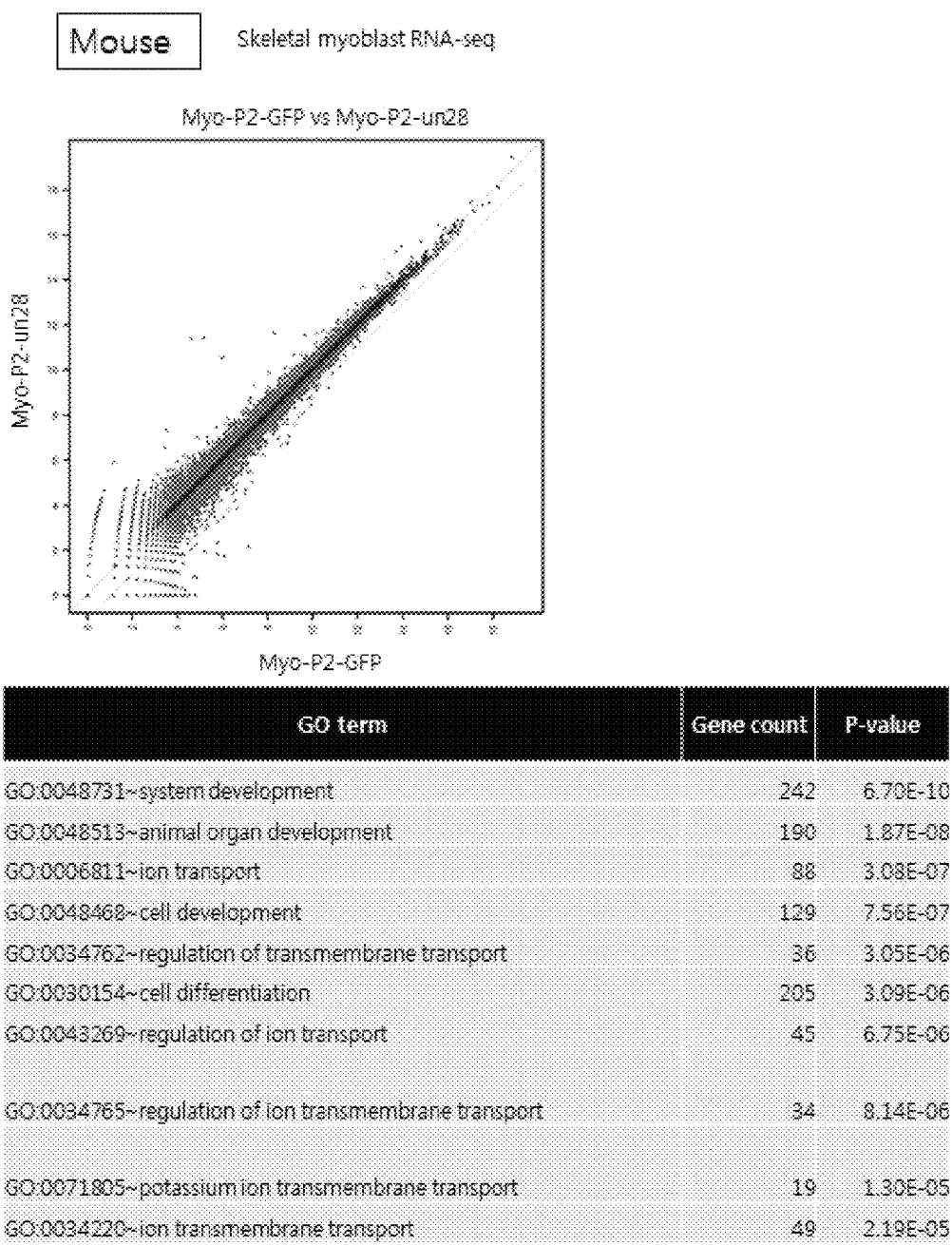

| GO term | Gene count | P-value |
|---|---|---|
| GO:0048731~system development | 242 | 6.70E-10 |
| GO:0048513~animal organ development | 190 | 1.87E-08 |
| GO:0006811~ion transport | 88 | 3.08E-07 |
| GO:0048468~cell development | 129 | 7.56E-07 |
| GO:0034762~regulation of transmembrane transport | 36 | 3.05E-06 |
| GO:0030154~cell differentiation | 205 | 3.09E-06 |
| GO:0043269~regulation of ion transport | 45 | 6.75E-06 |
| GO:0034765~regulation of ion transmembrane transport | 34 | 8.14E-06 |
| GO:0071805~potassium ion transmembrane transport | 19 | 1.30E-05 |
| GO:0034220~ion transmembrane transport | 49 | 2.19E-05 |

[FIG. 24B]

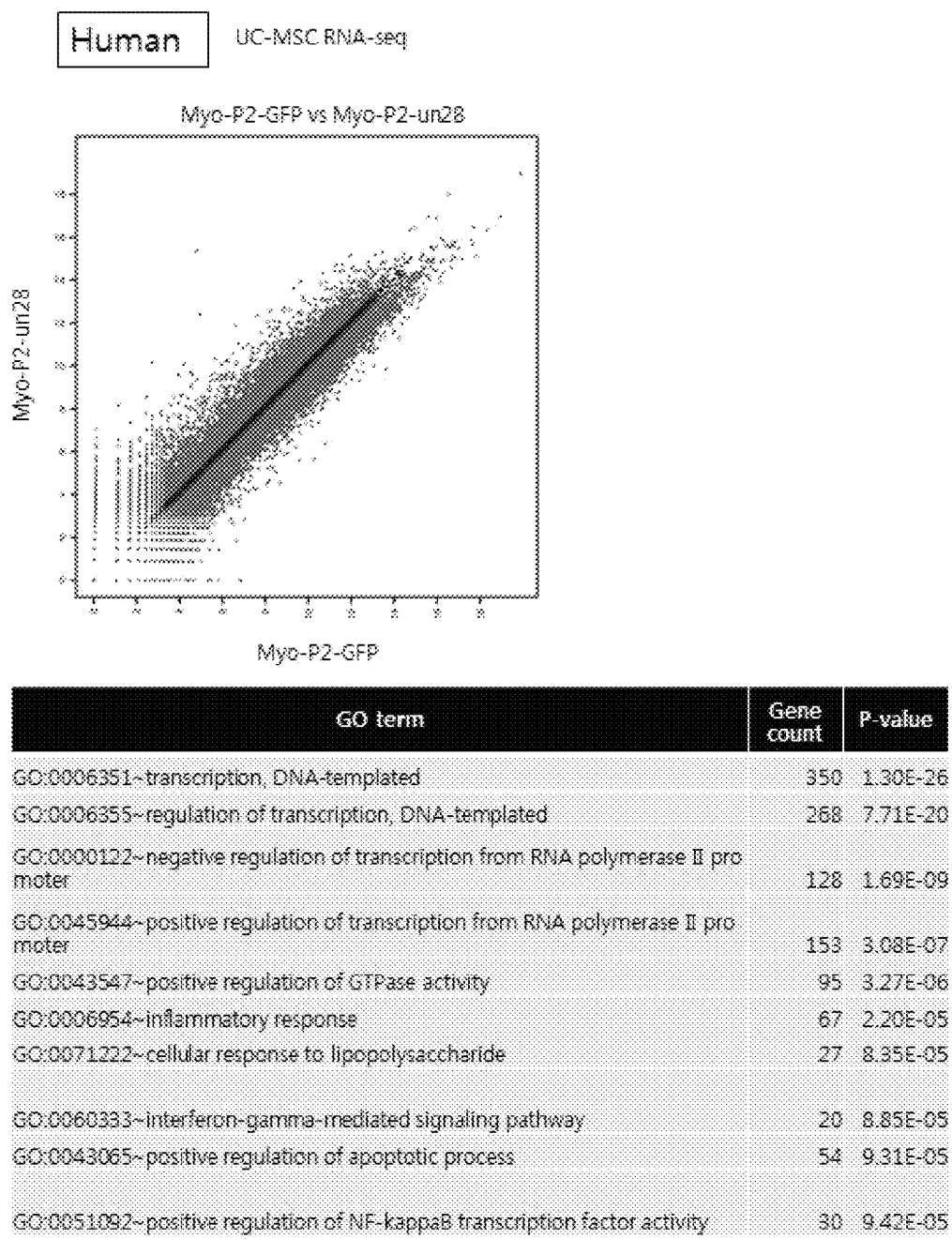

| GO term | Gene count | P-value |
|---|---|---|
| GO:0006351~transcription, DNA-templated | 350 | 1.30E-26 |
| GO:0006355~regulation of transcription, DNA-templated | 268 | 7.71E-20 |
| GO:0000122~negative regulation of transcription from RNA polymerase II promoter | 128 | 1.69E-09 |
| GO:0045944~positive regulation of transcription from RNA polymerase II promoter | 153 | 3.08E-07 |
| GO:0043547~positive regulation of GTPase activity | 95 | 3.27E-06 |
| GO:0006954~inflammatory response | 67 | 2.20E-05 |
| GO:0071222~cellular response to lipopolysaccharide | 27 | 8.35E-05 |
| GO:0060333~interferon-gamma-mediated signaling pathway | 20 | 8.85E-05 |
| GO:0043065~positive regulation of apoptotic process | 54 | 9.31E-05 |
| GO:0051092~positive regulation of NF-kappaB transcription factor activity | 30 | 9.42E-05 |

[FIG. 24C]

Shared GO in various stem cells over-expressing Lin28a DEG vs control

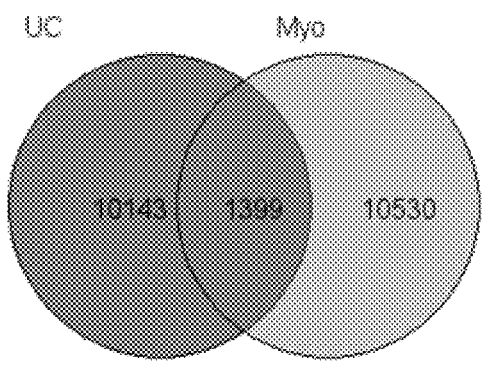

| GO term | Gene count | P-value |
|---|---|---|
| GO:0045944~positive regulation of transcription from RNA polymerase II promoter | 112 | 4.03E-09 |
| GO:0006954~inflammatory response | 51 | 3.86E-08 |
| GO:0007275~multicellular organism development | 111 | 4.77E-08 |
| GO:0006955~immune response | 42 | 2.39E-07 |
| GO:0007155~cell adhesion | 62 | 2.78E-07 |
| GO:0010628~positive regulation of gene expression | 54 | 3.03E-07 |
| GO:0002376~immune system process | 52 | 4.68E-07 |
| GO:0032496~response to lipopolysaccharide | 32 | 2.75E-06 |
| GO:0006811~ion transport | 67 | 4.09E-06 |
| GO:0030154~cell differentiation | 83 | 5.10E-06 |

METHOD USING EXPRESSION OF LIN28 FOR PREPARING STEM CELLS HAVING EXCELLENT RENEWAL ABILITY AND THERAPEUTIC CAPACITY

CROSS-REFERENCE TO RELATED APPLICATION

This application claims priority to and is a Continuation-In-Part of PCT/KR2017/000504 (WO2017/123065), filed on Jan. 13, 2017 entitled "METHOD USING EXPRESSION OF LIN28 FOR PREPARING STEM CELL HAVING EXCELLENT RENEWAL ABILITY AND DIFFERENTIATION POTENCY", which application claims priority to and the benefit of Korean Patent Application No. 10-2016-0004877, filed on Jan. 14, 2016, the disclosures of which are incorporated herein by reference in their entirety. Any disclaimer that may have occurred during the prosecution of the above-referenced applications is hereby expressly rescinded, and reconsideration of all relevant art is respectfully requested.

SEQUENCE STATEMENT

Incorporated by reference herein in its entirety is the Sequence Listing entitled "G18U10C0369PUS ST25-seq," created Sep. 21, 2018, size of 10 kilobyte.

TECHNICAL FIELD

The present invention relates to a method for preparing a stem cell blocking the loss of renewal ability and differentiation potency of a stem cell, including the step of subculturing a stem cell into which Lin28 has been introduced, a cell therapeutic agent comprising a stem cell expressing Lin28, a pharmaceutical composition comprising a neural stem cell expressing Lin28 for the prevention or treatment of a neurological disorder, a method for treating a neurological disorder using the composition, a pharmaceutical composition comprising a mesenchymal stem cell, a muscle stem cell, a fibroblast or a hematopoietic stem cell expressing Lin28 for the prevention or treatment of a muscular system disorder, a bone disorder, an epithelium-related disorder or a blood-related disorder, and a method for treating a muscular system disorder, a bone disorder, an epithelium-related disorder or a blood-related disorder using the composition.

BACKGROUND ART

A neural stem cell is usually an immature cell present in the nervous system, and is defined as a cell exhibiting self-renewal which continues to proliferate while being undifferentiated and exhibiting multipotency of differentiation, which is differentiation into a neuron and a neuroglia. The neural stem cell is present in various anatomical sites throughout the nervous system of a fetus of a mammal including a human, and recently, the neural stem cell is present not only in the fetus but also in a specific site of the adult nervous system, and the neural stem cell generates new neurons while continuing to proliferate in a specific site of the brain. In addition, it has been reported that the neural stem cell may also be differentiated from an embryonic stem cell which is a more immature cell, and may also be differentiated in other sites of the body, which are not the nervous system, that is, the bone marrow, the skin, the amniotic membrane, the umbilical cord blood cell, and the like, but the neural stem cell and the neuron cell derived from these tissues are extremely rare, and it is still not certain whether the neural stem cell is differentiated into a truly functional neuron. However, since the neural stem cell present in the nervous system is certainly differentiated into a functional neuron, recently, interest has been increased in not only basic studies on the proliferation and differentiation mechanism of a stem cell and the development of the nervous system, but also the possibility of a new cell and a new gene therapy by using biological characteristics of the neural stem cell in congenital and acquired intractable neurological disorders.

An intractable neurological disorder including Alzheimer's disease is a disease in which the neuron is degenerated and perishes, and until now, there is no fundamental therapeutic agent for most of the intractable neurological disorders. Accordingly, examples of a fundamental treatment method for an intractable neurological disorder include a method of normally recovering the function of a patient by removing the cause of a disease, or a method of suppressing the progression of the disease by diagnosing and treating the disease at the initial stage. Other treatment methods can partially recover the function of a damaged neuron, and a cell therapy using a neural stem cell under a situation in which a fundamental therapeutic agent is not present may suggest an alternative for various intractable neurologic al disorders.

Meanwhile, Lin28 is an important element which regulates the self-renewal, pluripotency, differentiation, and development of a embryonic stem cell. Further, in an embryonic stem cell expressing the Lin28 protein at a high level as a strong regulator of let-7 micro RNA (miRNA), it is known that let-7 miRNA is rarely expressed, and the expression of let-7 miRNA is increased when the expression of Lin28 is decreased after differentiation. In addition, in the related art, Lin28 has been used not only as an embryonic stem cell transcription factor but also as a reprogramming inducing factor.

References 1 and 2 to be described below disclose that Lin28 has effects of improving the proliferation of a neural progenitor cell (NSC), neurogenesis, or brain development, but they show effects of inducing the numerical proliferation of a neural progenitor cell and improving neurogenesis and brain development by regulating the expression of Lin28 present in an individual, and Reference Documents 1 and 2 do not disclose an influence of the introduction of an Lin28 gene suggested by the present invention on a dopaminergic neuron and effects of maintaining stem cell properties of a stem cell into which an Lin28 gene has been introduced, improving differentiation potency, the viability caused by suppressing an apoptotic cell death factor, and the like.

DISCLOSURE

Technical Problem

An object of the present invention is to provide a use of a stem cell expressing Lin28 as a cell therapeutic agent and a pharmaceutical use for the prevention or treatment of a neurological disorder, a muscular system disorder, a bone disorder, an epithelium-related disorder or a blood-related disorder.

Technical Solution

In order to achieve the object, the present invention provides a cell therapeutic agent including a stem cell expressing Lin28.

The present invention also provides a method for preparing a stem cell blocking the loss of renewal ability and differentiation potency of a stem cell, including the step of subculturing a stem cell into which Lin28 has been introduced. The present invention also provides a pharmaceutical composition including a neural stem cell expressing Lin28 for use in the prevention or treatment of a neurological disorder.

The present invention also provides a pharmaceutical composition including a mesenchymal stem cell, a muscle stem cell, a fibroblast or a hematopoietic cell expressing Lin28 for use in the prevention or treatment of a muscular system disorder, a bone disorder, an epithelium-related disorder or a blood-related disorder.

Advantageous Effects

The present invention can provide a stem cell which is cultured after introducing Lin28 or a vector expressing Lin28, which regulates an embryonic development process during stem cell culturing, and is excellent in terms of therapeutic effects during cell transplantation therapy by blocking the loss of renewal ability and differentiation potency generated during stem cell proliferation and subculturing.

DESCRIPTION OF DRAWINGS

FIG. 1A is a schematic diagram showing a process of isolating and culturing neural stem cells.

FIG. 1B is a result showing a correlation between differentiation potency of a stem cell and Lin28 by analyzing a decrease in differentiation potency to a dopaminergic neuron as the expression of endogenous Lin28 is decreased in a neural stem cell by real-time PCR.

FIG. 2A is a schematic diagram showing a process of isolating and culturing neural stem cells expressing Lin28.

FIG. 2B illustrates the results of observing the aspect of changes in various genes (Nestin, Sox2, Otx2, En-1, Foxa2 and Lmx1a) through real-time PCR by collecting cultured cells by introducing a vector expressing Lin28.

FIG. 2C illustrates the results of observing the aspect of changes in Foxa2 and Lmx1a genes through real-time PCR and an immunofluorescent staining method by collecting cultured cells by introducing a vector expressing Lin28.

FIG. 3A is a result of observing that a neural stem cell in which Lin28 is overexpressed has a better differentiation potency to neurons than a control.

FIG. 3B is a result of observing the effects of blocking the loss of differentiation potency of a neural stem cell in which Lin28 is overexpressed.

FIG. 3C illustrates the results of observing the morphologically and functionally mature of the dopaminergic neuron maintained by inducing the expression of Lin28.

FIG. 4A illustrates the results of observing the effects of suppressing apoptotic cell death of an Lin28 expression-induced neural stem cell and suppressing apoptotic cell death due to toxicity through an immunofluorescent staining method and flow cytometry.

FIG. 4B illustrates the results of observing the effects of suppressing apoptotic cell death of a dopaminergic neuron derived from an Lin28 expression-induced neural stem cell due to toxicity through the flow cytometry.

FIG. 4C illustrates the results of observing the effects of suppressing apoptotic cell death of a dopaminergic neuron derived from an Lin28 expression-induced neural stem cell due to toxicity through the TH fiber length and DA content.

FIG. 5A is a result illustrating the changes in animal behavior (rotation test) for 2 months after transplanting an Lin28 expression-induced neural stem cell into Parkinson model experimental animals.

FIG. 5B is a result illustrating the changes in animal behavior (stepping test) for 2 months after transplanting an Lin28 expression-induced neural stem cell into Parkinson model experimental animals.

FIG. 5C is a result illustrating the changes in animal behavior (cylinder test) for 2 months after transplanting an Lin28 expression-induced neural stem cell into Parkinson model experimental animals.

FIG. 5D is a result illustrating the transplantation lesion for 2 months after transplanting an Lin28 expression-induced neural stem cell into Parkinson model experimental animals.

FIG. 6A is a result of observing that an RNA-derived Lin28 was expressed 4 days after the introduction of the gene and the expression of Lin28 was suppressed 14 days after the introduction of the gene.

FIG. 6B is a result of identifying the degree of expression of Tuj1, GFAP, Foxa2, TH, Lmx1a, and Nurr1 through an immunofluorescent staining method after introducing Lin28 into the neural stem cell using RNA replicons.

FIG. 6C is a result of identifying the degree of expression of Foxa2, Tuj1, GFAP and TH through an real-time PCR after introducing Lin28 into the neural stem cell using RNA replicons.

FIG. 7A is a result of observing the cell proliferation effects in the 6th passage to 8th passage by introducing Lin28 into the 5th passage of a neural stem cell derived from a human embryonic stem cell using a lentiviral vector and then subculturing the neural stem cell.

FIG. 7B is a result of observing the apoptotic cell death decreasing effect and cell differential potency in the 6th passage to 8th passage by introducing Lin28 into the 5th passage of a neural stem cell derived from a human embryonic stem cell using a lentiviral vector and then subculturing the neural stem cell.

FIG. 8 is a result of identifying the osteogenic differentiation potency of a mesenchymal stem cell by staining the mesenchymal stem cell by ALP and Alizarin-red after introducing Lin28 into the mesenchymal stem cell isolated from a human bone marrow using RNA replicons and a result of identifying the degree of expression of an osteogenic differentiation factor through real-time PCR.

FIG. 9 is a result of identifying the degree of expression of a stemness factor and a differentiation gene of a mesenchymal stem cell through real-time PCR after introducing Lin28 in the 2rd passage of the mesenchymal stem cell isolated from a human bone marrow using a lentiviral vector.

FIG. 10 is a result of identifying the degree of expression of a factor associated with maintaining stem cell properties and an apoptotic cell death factor of a mesenchymal stem cell after introducing Lin28 in 2rd passage of the mesenchymal stem cell isolated from a human bone marrow using a lentiviral vector and the degree of expression of an osteogenic differentiation factor after the osteogenic differentiation of the mesenchymal stem cell in 1st passage and 4th passage through real-time PCR.

FIG. 11 is a results of observing the osteogenic differentiation potency of a mesenchymal stem cell in which the expression of Lin28 is induced 14 days after the osteogenic differentiation in 2th passage of the mesenchymal stem cell isolated from a human bone marrow through staining by ALP, Alizarin-red, and Safranin-O, respectively, and identifying the degree of expression of an osteogenic differentiation factor and a cartilage differentiation factor through real-time PCR.

FIG. 12 is a results of observing the osteogenic differentiation potency of a mesenchymal stem cell in which the expression of Lin28 is induced 14 days after the osteogenic differentiation in 3rd passage of the mesenchymal stem cell isolated from a human bone marrow through staining by ALP, Alizarin-red, and Safranin-O, respectively, and identifying the degree of expression of an osteogenic differentiation factor and a cartilage differentiation factor through real-time PCR.

FIG. 13 is a results of observing the osteogenic differentiation potency of a mesenchymal stem cell in which the expression of Lin28 is induced 14 days after the osteogenic differentiation in 4th passage of the mesenchymal stem cell isolated from a human bone marrow through staining by ALP, Alizarin-red, and Safranin-O, respectively, and identifying the degree of expression of an osteogenic differentiation factor and a cartilage differentiation factor through real-time PCR.

FIG. 14 is a result of identifying the cell proliferation ability of an umbilical cord mesenchymal stem cell in which the expression of Lin28 was induced.

FIG. 15A is a result of identifying the osteogenic potency of the mesenchymal stem cell and the degree of expression of a stemness factor and an osteogenic differentiation factor.

FIG. 15B is a result of identifying the osteogenic potency of the mesenchymal stem cell.

FIG. 16A is a schematic diagram showing a differentiation process of neural stem cells into muscle stem cell-specific progenitor cell in mouse.

FIG. 16B is a result of identifying the degree of expression of a muscle cell-specific factor in 2rd passage and 4th passage after introducing Lin28 into a muscle stem cell-specific progenitor cell isolated from a mouse using a lentiviral vector.

FIG. 16C is a result of identifying the number of muscle stem cell-specific progenitor cells after introducing Lin28 into a muscle stem cell-specific progenitor cell isolated from a mouse using a lentiviral vector.

FIG. 17 is a result of identifying the increase in number of the muscle stem cell-specific progenitor cells in the 6th passage to 13th passage after introducing Lin28 into a muscle stem cell-specific progenitor cell isolated from a mouse using a lentiviral vector.

FIG. 18A is a result of identifying the degree of differentiation of the muscle stem cell-specific progenitor cells using MF20 (myosin heavy chain) immunostaining and calculating the fusion index after introducing Lin28 into a muscle stem cell-specific progenitor cell isolated from a mouse using a lentiviral vector.

FIG. 18B is a result of identifying the degree of differentiation of the muscle stem cell-specific progenitor cells using muscle fiber of a muscle stem cell-specific progenitor cell after introducing Lin28 into the muscle stem cell-specific progenitor cell isolated from a mouse using a lentiviral vector.

FIG. 19A is a result of identifying the degree of expression of a muscle stem cell marker in the Nestin-CRE mouse model in which the expression of Lin28 was knocked out.

FIG. 19B is a result of identifying the body weight, the amount of muscle in the Nestin-CRE mouse model in which the expression of Lin28 was knocked out.

FIG. 20 is a result of observing the differentiation into tibialis anterior (TA) muscle cells and muscular fibrosis.

FIG. 21 is a result of observing the differentiation into gastrocnemius (GE) muscle cells and muscular fibrosis.

FIG. 22A is a result of identifying the number of epithelial progenitor cells and the degree of expression of an apoptotic cell death factor in 3rd, 5th, and 7th passages after introducing Lin28 into the epithelial progenitor cell isolated from a mouse using a lentiviral vector.

FIG. 22B is a result of identifying the degree of expression of the epithelial progenitor cell in 3rd, 5th, and 7th passages after introducing Lin28 into the epithelial progenitor cell isolated from a mouse using a lentiviral vector.

FIG. 23 is a result of identifying the maintenance of stemness properties of an umbilical cord mesenchymal stem cell in which the expression of Lin28 was induced.

FIG. 24A is a result of analyzing the cause of the effects of the expression of Lin28 at the genetic level in the mouse skeletal myoblast through RNA sequencing.

FIG. 24B is a result of analyzing the cause of the effects of the expression of Lin28 at the genetic level in human umbilical cord mesenchymal stem cell through RNA sequencing.

FIG. 24C is a result of analyzing the cause of the effects of the expression of Lin28 at the genetic level in human through RNA sequencing.

MODES OF THE INVENTION

The present invention provides a cell therapeutic agent including a stem cell expressing Lin28.

Lin28 is an important element which regulates the self-renewal, pluripotency, differentiation, and development of a stem cell. Further, in an embryonic stem cell expressing the Lin28 protein at a high level as a powerful regulator of let-7 micro RNA (miRNA), it is known that let-7 miRNA is rarely expressed, and the expression of let-7 miRNA is increased when the expression of Lin28 is decreased while differentiated. The changes in expression of Lin28 and let-7 miRNA are the same in most cells and tissues as well as the embryonic stem cells. In addition, in the related art, Lin28 has been used not only as an embryonic stem cell transcription factor but also as a reprogramming inducing factor, but the present inventors revealed that Lin28 or a vector expressing Lin28 can be introduced in order to prepare a stem cell excellent in terms of differentiation potency and renewal ability during stem cell culturing.

Specifically, in the following Examples, the present inventors observed that as the passage proceeds while a neural stem cell is isolated and cultured, differentiation potency to a dopaminergic neuron, an Lin28 gene, which regulates embryonic development, and Hmga2, which is a cell signaling substance, are remarkably decreased (FIG. 1). Thus, a neural stem cell expressing Lin28 was prepared by introducing a vector expressing Lin28 into a neural stem cell (FIG. 2). Since an Lin28 gene, which regulates embryonic development during neural stem cell culturing, may affect differentiation of the neural stem cell, as a result of subculturing the stem cell by inducing the expression of Lin28 only during the proliferation period by adding doxycycline which induces the expression of Lin28 thereto during the initial period of the culturing, it was confirmed that the loss of differentiation potency to a neuron cell is blocked by only introducing a vector expressing Lin28. Furthermore, it was observed that a dopaminergic neuron maintained by inducing the expression of Lin28 was morphologically and functionally mature (FIG. 3).

During neural stem cell culturing, as the passage proceeds, apoptotic cell death is increased, which causes a decrease in renewal ability during stem cell transplantation treatment. Most dopaminergic neurons derived from neural stem cells in which the expression of Lin28 was not induced was destroyed by the toxin $H_2O_2$, whereas a dopaminergic neuron derived from a neural stem cell in which the expression of Lin28 was induced exhibited a protective effect against the toxin $H_2O_2$ (FIG. 4).

Finally, as a result of carrying out an experiment on the renewal ability of a neural stem cell expressing Lin28 in a Parkinson model rat, it was confirmed that an excellent effect against Parkinson's disease was exhibited and a larger amount of dopaminergic neurons survived in a group transplanted with a neural stem cell in which the expression of Lin28 was induced (FIG. 5).

Accordingly, the present invention provides a cell therapeutic agent including a stem cell expressing Lin28, a method for preparing a stem cell, which blocks the loss of renewal ability and differentiation potency of a stem cell, including the step of subculturing a stem cell into which Lin28 has been introduced, a pharmaceutical composition including a neural stem cell expressing Lin28 for the treatment of a neurological disorder, a method for treating a neurological disorder, including the step of administering the composition to a subject, and a novel use of Lin28 for preparing a stem cell in which the loss of renewal ability and differentiation potency is blocked during stem cell proliferation and subculturing.

The Lin28 is present in two forms, Lin28 homolog A (Lin28a) and B (Lin28b), in a mammal such as a rat and a human. In the present invention, the Lin28 has a publicly-known sequence of Lin28a. In the present invention, a nucleic acid sequence of the human Lin28a is set forth in SEQ ID No. 1, and a nucleic acid sequence of the rat Lin28a is set forth in SEQ ID No. 2.

In the present invention, the stem cell may include an embryonic stem cell or an adult stem cell. In a specific exemplary embodiment, the adult stem cell may be a neural stem cell, a mesenchymal stem cell, a muscle stem cell, a fibroblast or a hematopoietic stem cell. In another specific exemplary embodiment, in addition to the stem cells listed above, the stem cell may also include a progenitor cell capable of being differentiated depending on the stimulus, and may include a muscle stem cell-specific progenitor cell and an epithelial progenitor cell, but is not limited thereto.

A neural stem cell (NSC) is a cell which is capable of self-renewal and has differentiation potency to a nervous system cell. It has been reported that the neural stem cell is differentiated into a neuron, an astrocyte, and an oligodendrocyte. Further, a mesenchymal stem cell is a cell which may be differentiated into a cell such as a fat cell, a bone cell, and a cartilage cell.

In the present invention, the neural stem cell may be isolated from the mesencephalon, bone marrow, or the like, and an autologous or allogeneic neural stem cell may be used. For example, it is possible to minimize an immune rejection response among individuals by collecting a neural stem cell directly from a patient or isolating and using a neural stem cell from bone marrow which coincides with a human leukocyte antigen (HLA) type using a database of a blood bank. In addition, as with the neural stem cell, for the mesenchymal stem cell, an autologous or allogenic mesenchymal cell may be used, and the mesenchymal stem cell may be obtained from bone marrow, tissue, embryo, umbilical cord blood, blood or body fluids. The mesenchymal stem cell may be obtained by a method for obtaining a mesenchymal stem cell from a mesenchymal stem cell supply source, and a method publicly known in the art. Also, as with the neural stem cell and the mesenchymal stem cell, for the muscle stem cell, the fibroblast or the hematopoietic stem cell, an autologous or allogenic cell may be used.

Accordingly, the present invention may provide an excellent therapeutic effect during stem cell transplantation for the treatment of a disorder by introducing Lin28, which regulates an embryonic development process, in the form of a gene into a stem cell, expressing Lin28 during culturing, and blocking the loss of differentiation potency to various tissue cells generated during stem cell proliferation and subculturing and renewal ability.

In the present invention, a time point for introducing an Lin28 gene during culturing of a stem cell expressing Lin28 is not fixed, and the stem cell expressing Lin28 may be obtained, for example, by, after introducing the Lin28 gene into an isolated stem cell, proliferating and differentiating the stem cell under appropriate conditions in a test tube, or by sufficiently proliferating the stem cell, and then introducing the Lin28 gene thereinto.

In the present invention, the stem cell expressing Lin28 may be a stem cell into which a vector expressing Lin28 has been introduced.

In the present invention, the "vector" refers to a gene construct including foreign DNA inserted into a genome encoding a polypeptide. The vector is a vector in which a nucleic acid sequence of Lin28 is inserted into a genome, and these vectors may be, for example, a DNA vector, a plasmid vector, a cosmid vector, a bacteriophage vector, a yeast vector, a viral vector, or an RNA replicon, but are not limited thereto.

For example, the vector may be a virus vector, a plasmid vector, or an RNA replicon. As an example of the viral vector, an adenovirus, a retrovirus, an adeno-associated virus, a herpes simplex virus, SV40, a polyomavirus, a papillomavirus, a picornavirus, a vacciniavirus, a helper dependent adenovirus, or the like may be used as a mediator expressing Lin28. The viruses may be a recombinant virus.

In the present invention, 'replicon' refers to a DNA or RNA region which is replicated from one replication origin.

In exemplary embodiments of the present invention, as the viral vector expressing Lin28, a lentiviral vector was used for introduction into a stem cell, but the viral vector is not limited thereto.

In an exemplary embodiment of the present invention, an RNA replicon expressing Lin28 was used for introduction into a stem cell. When Lin28 is introduced into a cell by using an RNA replicon, the Lin28 gene automatically vanishes within about two weeks after introduction, so that it may be preferred in that the step of adjusting the expression of Lin28 is not needed.

In one specific exemplary embodiment of the present invention, the vector expressing Lin28 may be an adenovirus. The adenovirus disappears about 8 days after introduction in vivo, and thus may be preferred in that the step of regulating the expression of the Lin28 gene is not additionally needed.

In the present invention, a suitable expression vector includes a signal sequence or leader sequence for membrane targeting or secretion in addition to expression regulatory elements, such as a promoter, an operator, an initiation codon, a termination codon, a polyadenylation signal and an enhancer, and may be prepared variously according to purpose. The promoter of the vector may be constitutive or inducible. Further, the expression vector includes a selectable marker for selecting a host cell containing a vector, and includes a replication origin in the case of being a replicable expression vector.

In one specific exemplary embodiment, when the Lin28 gene is expressed through the viral or plasmid vector, the step of being able to adjust the expression of the Lin28 gene may be additionally included.

The Lin28 gene to be introduced into the vector may be a nucleic acid sequence encoding an Lin28 protein or an analog having characteristics functionally equivalent thereto. The nucleic acid may be DNA or RNA. In the present specification, an analog having characteristics functionally equivalent is an analog having characteristics functionally equivalent to the Lin28, and specifically, refers to a peptide in which some amino acid residues among the peptides are substituted, deleted, or added.

Meanwhile, when the expression of Lin28 is continuously induced, there is a risk that the differentiation potency is decreased by interference with differentiation into various tissue cells and an oncogene is generated, so that the step of being able to adjust the expression of the Lin28 gene may be needed. As previously described, an adenovirus as a vector expressing Lin28 disappears about 8 days after introduction in vivo, and when an RNA replicon is used, a gene automatically vanishes within about 2 weeks, so that the two cases may be preferred in that the step of adjusting the expression of the Lin28 gene is not additionally needed.

In one specific exemplary embodiment, the expression of the Lin28 may be on and off by a treatment with a specific material, and the specific material is not limited as long as the specific material enables the expression of the Lin28 to be on and off. In an exemplary embodiment of the present invention, for example, the expression of Lin28 introduced into a lentivirus may be adjusted by doxycycline.

In addition, in the present invention, as a method for introducing a vector expressing Lin28 into a stem cell, a publicly-known transduction or transfection method may be used, and for example, a centrifugation method, a microinjection method, a calcium phosphate precipitation method, an electroporation method, a liposome-mediated transfection method, a DEAE-dextran treatment method, gene bombardment, and the like may be exemplified, but the method is not limited thereto.

A composition of the present invention exhibits a prophylactic or therapeutic effect on a neurological disorder, a muscular system disorder, a bone disorder, an epithelium related disorder or a blood-related disorder. The neurological disorder of the present invention may include a degenerative neurological disorder, and examples thereof include various neurological disorders including Parkinson's disease, dementia, Alzheimer's disease, Huntington's disease, amyotrophic lateral sclerosis, memory loss, myasthenia gravis, progressive supranuclear palsy, multiple system atrophy, essential tremor, cortical-basal ganglionic degeneration, diffuse Lewy body disease, and Pick's disease. The muscular system disorder includes muscular system disorders such as muscular dystrophy, cerebral palsy, fibrodysplasia ossificans progressiva, dermatomyositis, compartment syndrome, myasthenia gravis, amyotrophic lateral sclerosis, mitochondrial myopathy, rhabdomyolysis, polymyositis, fibromyalgia, myotonia, and myofascial pain syndrome. The bone disorder includes bone disorders such as osteomalacia, osteoporosis, and rickets, and the epithelium related disorder include disorders such as intractable conical disease. The blood-related disorder includes blood-related disorders such as leukemia, anemia, lymphoma or multiple myeloma. A pharmaceutical composition according to the present invention may be applied to all the disorders which can be treated through transplantation of a stem cell in addition to the above disorders.

Accordingly, the present invention provides a cell therapeutic agent including a stem cell expressing Lin28, a pharmaceutical composition including a neural stem cell, a mesenchymal stem cell, a muscle stem cell, a fibroblast or a hematopoietic stem cell expressing Lin28 for use in the prevention or treatment of a neurological disorder, a muscular system disorder, a bone disorder, an epithelium-related disorder or a blood-related disorder and a method for treating a neurological disorder, a muscular system disorder, a bone disorder, an epithelium-related disorder or a blood-related disorder, including administering the same to a subject.

In the present invention, "treatment" refers to all the actions that suppress or alleviate or advantageously alter clinical situations related to a disorder. Furthermore, the treatment may refer to increased survival as compared to an expected survival rate when the treatment is not received. The treatment simultaneously includes prophylactic means in addition to therapeutic means.

In the present specification, "subject" may be a vertebrate, preferably, a mammal, for example, a dog, a cat, a rat, a human, or the like, which is a target of treatment, observation or an experiment.

The composition of the present invention may be applied as a cell therapeutic agent and may be formulated by additionally including a pharmaceutically acceptable carrier. In the present invention, the term "pharmaceutically acceptable carrier" refers to a carrier or diluent that does not significantly stimulate an organism and does not inhibit the biological activity or properties of an administered ingredient. In the present invention, for the composition of the present invention, which may be applied as a cell therapeutic agent, the pharmaceutically acceptable carrier may be used without limitation as long as the pharmaceutically acceptable carrier is publicly known in the art, such as a buffering agent, a preservative, an anesthetizing agent, a solubilizing agent, an isotonic agent, a stabilizer, a base substance, an excipient, and a lubricant. The pharmaceutical composition of the present invention may be prepared by a technique which is applicable to various formulations forms. The cell therapeutic agent which is the composition of the present invention can be administered through any route as long as the cell therapeutic agent can induce migration to a disease site. It is also possible to take into consideration a method of loading the cell therapeutic agent into a vehicle including a means for directing a stem cell to a lesion in some cases. Accordingly, the composition of the present invention may be administered via various routes including topical (including buccal, sublingual, dermal, and intraocular administration), parenteral (including subcutaneous, intradermal, intramuscular, intravascular, intraarticular, and intracerebrospinal fluid administration), or transdermal administration, and preferably, is administered directly to a disease site. As an aspect, a stem cell may be drug suspended in a suitable diluent and administered to an individual, and the diluent is used for the use of protecting and maintaining the cell and facilitating the use during the injection into a target tissue. The diluent may be physiological saline, a buffer solution such as a phosphate buffer solution and HBSS, a cerebrospinal fluid, and the like. Further, the pharmaceutical composition may be administered by any device such that an active material may be transferred to a target cell. A preferred mode of administration and formulation is an injection. The injection may be prepared by using an aqueous solvent such as physiological saline, Ringer's solution, Hank's solution or a sterile aqueous solution, a vegetable oil such as olive oil, a higher fatty acid ester such as ethyl oleate, a non-aqueous solvent such as ethanol, benzyl alcohol, propylene glycol, polyethylene glycol, or glycerin, and the like, and for transmucosal administration, a non-invasive agent publicly known in the art, which is suitable for a barrier through which the injection is to be passed, may be used, and the injection may additionally include a pharmaceutical carrier such as ascorbic acid, sodium hydrogen sulfite, BHA, a tocopherol, EDTA, and the like as a stabilizer for preventing degeneration, an emulsifier, a buffering agent for pH control, and a preservative for inhibiting microbial growth, such as phenylmercury nitrate, thimerosal, benzalkonium chloride, phenol, cresol, and benzyl alcohol.

In the present invention, the term "cell therapeutic agent" refers to a drug for administering a genetic material or a cell into which a genetic material has been transferred to the human body for the purpose of treating a disease or the like.

In the present invention, the term "administration" refers to administration of the composition of the present invention to a patient by any appropriate method, and for the route of administration of the composition of the present invention, the composition of the present invention may be administered via various routes of oral or parenteral administration, which may reach a target tissue. The route of administration may be intraperitoneal administration, intravenous administration, intramuscular administration, subcutaneous administration, intradermal administration, oral administration, topical administration, intranasal administration, intrapulmonary administration, and rectal administration, but is not limited thereto.

In the present specification, "effective amount" refers to an amount required to delay or completely stop the onset or progression of a specific disease to be treated. In the present invention, the composition may be administered in a pharmaceutically effective amount. It is obvious to a person skilled in the art that a suitable total usage amount per day may be determined by a doctor within the scope of sound medical judgment.

For the purpose of the present invention, it is preferred that a specific therapeutically effective amount for a specific patient is differently applied depending on various factors including the type and extent of a response to be achieved, a specific composition including whether different formulations are used according to the case, the age, body weight, general health status, gender, and diet of the patient, the time of administration, the route of administration, the secretion rate of the composition, the period of treatment, a drug used in combination with or concurrently with the specific composition and similar factors well known in the medical field.

Further, the present invention provides a method for preparing a stem cell blocking the loss of renewal ability and differentiation potency of a stem cell, including the step of subculturing a stem cell into which Lin28 has been introduced.

In the method for preparing a stem cell according to the present invention, the stem cell to which Lin28 has been introduced may be a stem cell to which a vector expressing Lin28 has been introduced.

In the method for preparing a stem cell, all the contents described above may be applied as they are or applied mutatis mutandis to a stem cell, a vector expressing Lin28, and a stem cell expressing Lin28 (to which Lin28 has been introduced).

In general, during stem cell proliferation and subculturing, proliferation potency and differentiation potency are reduced, and renewal ability (regenerative potential), which restores tissue damage at the time of transplantation, but the method for preparing a stem cell according to the present invention has an effect of blocking the loss of proliferation potency, renewal ability, and differentiation potency even through the passage of stem cells is increased, so that it is possible to exhibit an excellent therapeutic effect during the stem cell transplantation treatment.

MODE FOR INVENTION

Hereinafter, the present application will be described in detail through the Examples. The following Examples are provided only for exemplifying the present application, and the scope of the present application is not limited to the following Examples.

[Example 1] Preparation of Neural Stem Cell Expressing Lin28 Using Viral Vector

A neural stem cell (VM-NSC) was isolated from the ventral midbrain (VM) of a Hsd:ICR (CD-1) fetus (embryonic day 10) and cultured. In the initial period (day 2 to 3) of the culture, the neural stem cell was proliferated and cultured after introducing a doxycycline-inducible lentiviral vector (Buganim et al Cell. 2012 Sep. 14; 150(6):1209-22. doi: 10.1016/j.cell.2012.08.023.) inducing the expression of Lin28 (Dox-on system) into the cell using Lin28 of SEQ ID No. 2. During the proliferation and culture, a neural stem cell expressing Lin28 was prepared by adding doxycycline thereto and inducing the expression of the Lin28 gene in the VM-NSC.

[Experimental Example 1] Experiment of Identifying Differentiation Potency to Dopaminergic Neuron During the isolation and culturing of a neural stem cell (VM-NSC) from the ventral midbrain (VM) of a Hsd:ICR (CD-1) fetus (mouse embryonic day 10), the differentiation potency of the neural stem cell was observed through a real-time PCR analysis. The results are illustrated in FIG. 1.

As illustrated in FIG. 1, it could be observed that during the isolation and culturing of the neural stem cell, as the passage proceeded, the differentiation potency to a dopaminergic neuron was remarkably decreased. Further, it could be confirmed that during the culturing procedure, an Lin28 gene, which regulates embryonic development, was decreased, Hmga2, which is a cell signaling substance, was remarkably decreased, and let-7b micro RNA was increased.

[Experimental Example 2] Experiment of Identifying Aspect of Change in Gene of Dopaminergic Neuron Proliferated and Cultured after Introducing Lin28 Gene The aspects of changes in various genes were analyzed and observed through real-time PCR and an immunofluorescent staining method by collecting cells cultured each passage three days after the introduction of a lentiviral vector expressing an Lin28 into a neural stem cell by proliferating and culturing the lentiviral vector expressing an Lin28 gene after introducing the lentiviral vector into the stem cell. The results are illustrated in FIG. 2.

As illustrated in FIG. 2, it was confirmed that during the culturing period, the synthesis of Nestin and Sox2, which are neural stem cell-specific genes, and Otx2, En-1, Foxa2, and Lmx1a, which are dopaminergic neuron-specific genes had been greatly decreased, whereas a phenomenon of the decrease in synthesis of the genes was prevented in a group into which the Lin28 gene had been introduced.

[Experimental Example 3] Experiment of Identifying Differentiation Potency of Neural Stem Cell after Inducing Expression of Lin28

During the initial period of culturing the neural stem cell, for the ventral midbrain-neural stem cell (VM-NSC) proliferated by adding doxycycline thereto, the differentiation potency of the neural stem cell was observed through an immunofluorescent staining method in a state where the expression of Lin28 was blocked without adding doxycycline after the expression of Lin28 was induced. The results are illustrated in FIG. 3.

As illustrated in FIGS. 3A to 3J, it could be confirmed that during the proliferation period, the loss of differentiation potency to a neuron was blocked by only introducing a vector expressing Lin28. Further, as illustrated in K to V, it was confirmed that the induction of the expression of Lin28 suppressed the loss of differentiation potency to a dopaminergic neuron, and the dopaminergic neurons all became co-labeled with a midbrain-specific marker. It was confirmed that the dopaminergic neuron maintained by inducing the expression of Lin28 was morphologically and functionally mature (W, X and Y).

[Experimental Example 4] Experiment of Identifying Effects of Suppressing Apoptotic Cell Death of Dopaminergic Neuron During neural stem cell culturing, apoptotic cell death, which is increased as the passage proceeds, is known to be responsible for causing a decrease in renewal ability during stem cell transplantation treatment. Thus, an effect that the expression of Lin28 in the neural stem cell suppresses apoptotic cell death was observed through an immunofluorescent staining method and flow cytometry. The results are illustrated in FIG. 4.

As illustrated in FIG. 4, it was confirmed that most of the dopaminergic neurons derived from neural stem cells in which the expression of Lin28 was not induced were destroyed by the toxin $H_2O_2$, whereas a dopaminergic neuron derived from a neural stem cell in which the expression of Lin28 was induced exhibited a protective effect against the toxin $H_2O_2$. Accordingly, it is possible to expect that the expression of Lin28 may prevent the phenomenon of a reduction in renewal ability which may be generated during cell transplantation treatment.

[Experimental Example 5] Experiment of Identifying Therapeutic Effect of Neural Stem Cell Expressing Lin28

After a neural stem cell in which the expression of Lin28 was induced was transplanted into a striatum of a hemi-Parkinson model rat by using 6-hydroxydopamine (6-OHDA), a change in animal behavior was measured. The 6-OHDA is a neural toxin widely used in the preparation of a Parkinson's disease animal model, and exhibits toxicity specific for a dopaminergic neuron. The results are illustrated in FIG. 5.

As illustrated in FIG. 5, the Parkinson model rat, which was transplanted with a neural stem cell in which the expression of Lin28 was induced, exhibited an excellent therapeutic effect when compared to a control. When data of analyzing a transplantation lesion 2 months after the transplantation of the neural stem cell was identified, it could be confirmed that a greater amount of dopaminergic neurons survived in a transplantation specimen of a group transplanted with a neural stem cell in which the expression of Lin28 was induced, and that the surviving dopaminergic neurons were co-labeled with a midbrain specific marker.

[Example 2] Preparation of Neural Stem Cell Expressing Lin28 Using RNA Replicon System A neural stem cell was isolated from the midbrain of a Hsd:ICR(CD-1) fetus and cultured. During the initial period of the culture, the neural stem cell was proliferated and cultured after introducing a Lin28 replicon inducing the expression of Lin28 using Lin28 of SEQ ID No. 2. During the proliferation and culturing, a neural stem cell expressing Lin28 was prepared by adding Lipofectamine thereto.

[Experimental Example 6] Identification of Differentiation and Proliferation Potency of Neural Stem Cell into which Lin28 RNA Gene has been Introduced Since the Lin28 gene automatically vanishes within 14 days after the introduction of the neural stem cell prepared in Example 2, Lin28 automatically vanished after the expression of Lin28 was induced, so that the differentiation potency of the neural stem cell was observed by an immunofluorescent staining method in a state where the expression of Lin28 was blocked. The results are illustrated in FIG. 6.

As illustrated in FIG. 6, it could be confirmed that an RNA-derived Lin28 was expressed 4 days after the introduction of the gene (A), and it could be confirmed that the expression of Lin28 was suppressed 14 days after the introduction of the gene (B). Further, it was confirmed that the expression of Lin28 was maintained during the 3rd passage, and a cell group expressing Lin28 had proliferated to a larger amount of cells (C).

As a result of identifying the degree of expression of Tuj1, GFAP, Foxa2, TH, Lmx1a, and Nurr1 through an immunofluorescent staining method (D to Q), it could be confirmed that when the differentiation was induced by introducing Lin28 into the neural stem cell using an RNA replicon system, the neurons were increased (Tuj1), differentiation into an astrocyte was suppressed (GFAP), and the expression of Foxa2, TH, Lmx1a, and Nurr1, which are midbrain dopaminergic factors, was maintained.

[Example 3] Preparation of Human Embryonic Stem Cell-Derived Neural Stem Cell Expressing Lin28 Using Viral Vector A neural stem cell was isolated from a human embryonic stem cell and cultured. During the initial period of the culture, the neural stem cell was proliferated and cultured after introducing a doxycycline-inducible lentiviral vector inducing the expression of Lin28 into the cell using Lin28 of SEQ ID No. 1. During the proliferation and culturing, a human embryonic cell-derived neural stem cell expressing Lin28 was cultured by adding doxycycline thereto to induce the expression of the Lin28 gene in the neural stem cell.

[Experimental Example 7] Identification of Differentiation Potency of Human Embryonic Cell-Derived Neural Stem Cell in which Expression of Lin28 is Induced to Dopaminergic Neuron After the neural stem cell prepared in Example 3 was subcultured at an interval of 6 days by introducing a lentiviral virus expressing Lin28 in the 5th passage, the effect of proliferating to a large amount was observed in the 6th passage to 8th passage, and is illustrated in FIG. 7.

As illustrated in FIG. 7A, it can be seen that the cells are proliferated until the 6th passage to 8th passage, and it can be confirmed that apoptotic cell death is decreased through U to W, and the differentiation potency to the dopaminergic neuron is improved through X to Z (FIG. 7B).

[Example 4] Preparation of Mesenchymal Stem Cell Expressing Lin28 Using RNA Replicon System A mesenchymal stem cell was isolated from a human bone marrow and cultured. During the initial period of the culture, the mesenchymal stem cell was proliferated and cultured after introducing a Lin28 replicon inducing the expression of Lin28 using Lin28 of SEQ ID No. 1. During the proliferation and culturing, a mesenchymal stem cell expressing Lin28 was prepared by adding RNA replicon expressing Lin28 thereto.

[Experimental Example 8] Identification of Differentiation Potency of Mesenchymal Stem Cell into which Lin28 RNA Gene has been Introduced Since the Lin28 gene automatically vanishes within 14 days after the introduction of the gene in the mesenchymal stem cell prepared in Example 4, Lin28 vanished after the expression of Lin28 was induced, so that the osteogenic differentiation potency of the mesenchymal stem cell was observed through staining with ALP and Alizarin-red in a state where the expression was blocked. Further, the degree of expression of Runx2, COL1A1, BSP, OCN, and Osterix, which are osteogenic differentiation factors, were identified by using real-time PCR. The results are illustrated in FIG. 8.

In FIG. 8, it was confirmed that Lin28 derived from RNA was expressed 4 days after the introduction of Lin28 (Expansion of FIG. 8), and that the osteogenic differentiation potency was improved through the enhancement of expression of Runx2, COL1A1, BSP, OCN, and Osterix, which are osteogenic differentiation factors, in an Lin28 expression-induced experimental group 14 days after the osteogenic differentiation.

[Example 5] Preparation of Mesenchymal Stem Cell Expressing Lin28 Using Viral Vector A mesenchymal stem cell was isolated from a human bone marrow and cultured. The mesenchymal stem cell was proliferated and cultured after introducing a doxycycline-inducible lentiviral vector inducing the expression of Lin28 in the 1st passage using Lin28 of SEQ ID No. 1. During the proliferation and culture, a mesenchymal stem cell expressing Lin28 was prepared by adding doxycycline thereto and inducing the expression of the Lin28 gene in the mesenchymal stem cell.

[Experimental Example 9] Identification of Stem Cell Properties of Mesenchymal Stem Cell in which Expression of Lin28 is Induced In the 2rd passage of the mesenchymal stem cell prepared in Example 5, the degree of expression of stemness factors and differentiation genes of the mesenchymal stem cell in which the expression of Lin28 was induced was identified through real-time PCR, and is illustrated in FIG. 9.

As illustrated in FIG. 9, through the fact that in the mesenchymal stem cell in which the expression of Lin28 was induced, the expression of Nanog and Oct4, which are stemness factors, were enhanced and simultaneously, the expression of Cox2, SMA, and Stella, which are differentiation factors, was suppressed, it was confirmed that the stem cell properties of the mesenchymal stem cell were maintained.

[Experimental Example 10] Identification of Degree of Expression of Stemness Maintenance Genes and Osteogenic Differentiation Factors In the 2rd passage of the mesenchymal stem cell prepared in Example 5, the degree of expression of stemness maintenance genes and apoptotic cell death factors of the mesenchymal stem cell in which the expression of Lin28 was induced and the degree of expression of osteogenic factors after the osteogenic differentiation of the mesenchymal stem cell in the 1st passage and the 4th passage after the expression of Lin28 were identified through real-time PCR, and are illustrated in FIG. 10.

In FIG. 10A, it could be confirmed that in the step of proliferating the mesenchymal stem cell, the mesenchymal stem cell in which Lin28 was expressed maintained the expression level of stemness factors (Oct4 and Nanog) and suppressed the expression of an apoptotic cell death factor (P16), and in FIG. 10B, it could be confirmed that after the differentiation, OCN and Runx2, which are osteogenic factors, were expressed in in the mesenchymal stem cells in the 1st passage and the 4th passage.

[Experimental Example 11] Identification of Osteogenic Differentiation of Mesenchymal Stem Cell Expressing Lin28

1) Identification of Osteogenic Differentiation Potency of Mesenchymal Stem Cell in 2rd and 3th Passages In the 2rd passage and the 3th passage of the mesenchymal stem cell prepared in Example 5, the osteogenic differentiation potency of the mesenchymal stem cell in which the expression of Lin28 was induced 14 days after the osteogenic differentiation was observed through staining with ALP and Alizarin-red and the degree of expression of the osteogenic differentiation factor was identified through real-time PCR, and are illustrated in FIGS. 11 (2rd passage) and 12 (3th passage).

As illustrated in FIGS. 11 and 12, as a result of staining both the 2rd passage and the 3th passage with ALP and Alizarin-red 14 days after the osteogenic differentiation, it could be confirmed that the osteogenic differentiation potency was improved. Further, it was confirmed that the expression of Runx2, COL1A1, BSP, OCN, and Osterix, which are osteogenic differentiation factors, was remarkably increased as compared to a control.

2) Identification of Osteogenic Differentiation Potency of Mesenchymal Stem Cell in 4th Passage In the 4th passage of the mesenchymal stem cell prepared in Example 5, the osteogenic differentiation potency of the mesenchymal stem cell in which the expression of Lin28 was induced 14 days after the osteogenic differentiation was observed through staining with Safranin-O and the degree of expression of the cartilage differentiation factors was identified through real-time PCR, and are illustrated in FIG. 13.

As illustrated in FIG. 13, as a result of staining with Safranin-O 14 days after the osteogenic differentiation of the mesenchymal stem cell in the 4th passage, it could be observed that the cartilage differentiation potency was improved. Furthermore, it was confirmed that the expression of Aggrecan, COL2, and SOX9, which are cartilage differentiation factors, was remarkably increased as compared to a control.

[Example 6] Preparation of Human Umbilical Cord Mesenchymal Stem Cell Expressing Lin28 Using Viral Vector Human umbilical cord mesenchymal stem cells (UC-MSC) were obtained from Samsung Hospital. UC-MSC was cultured in α-MEM supplemented with 10% FBS with media change every other day. The cells were passaged when reaching ~80% confluence using TrypLE (Gibco) and replated in the density 5000 cells/cm$^2$. The level of population doubling was calculated using the formula: x=[log 10(NH)−log 10(NI)]/log 10(2), where NI is the number of inoculum cells number and NH is the number of harvested cells. The UC-MSC was expanded until it reached senescence.

[Experimental Example 12] Identification of In Vivo Osteogenesis of Human Umbilical Cord Mesenchymal Stem Cell Expressing Lin28

In vivo osteogenicity was assessed using a critical calvarial defect assay. Briefly, a 14-week old Sprague-Dawley (250-300 g) rat was anesthetized using a mixture of Zoletil: Rompun at a 2:1 ratio at 1 μl/gr of the body weight. Then a midline calvarial incision was made, the subcutaneous fascia was divided, and periosteum was exposed. Full-thickness circular defects of 4 mm were made in the left parietal bones using a dental trephine and cleaned of any debris using sterile PBS. UC-MSC during the expansion period was implanted using Tisseel fibrin glue as a scaffold. Briefly, 1.5×10$^6$ cells were resuspended in 20 μl Fibrinogen and mixed with 20 μl Thrombin until fibrin polymerization was completed. The cells-fibrin polymer gel was then implanted into the calvarial defect area and covered with a poly-L-lactone membrane. After 8 weeks, the rats were sacrificed using $CO_2$ asphyxiation. The calvarial bone was extracted, trimmed, and fixed in 4% paraformaldehyde for 24 h at 4° C. The samples were scanned using a micro-CT system (Quantum FX μCT). Three-dimensional images were reconstructed, and the local density and volume of the defects within the regenerated bone were calculated.

Osteogenic differentiation was induced when UC-MSC reached confluency by switching to osteogenic induction media (α-MEM, 10% FBS, 10 nM Dexamethasone, 100 μg/ml Ascorbic acid, β-glycerophosphate) for 2 weeks with media change every other day. At the end of induction, the osteogenic cells were fixed in 4% PFA for 10 minutes and visualized using 2% Alizarin red.

From the Experimental Example 9 to 11, it was confirmed that the stem cell properties of the mesenchymal stem cells expressing Lin28 were maintained and differentiation into bone was enhanced. Similarly, proliferation of mesenchymal stem cells derived from the umbilical cord was increased (FIG. 14), and bone formation was increased upon induction of differentiation into bone cells (FIG. 15). In addition, it confirmed that the expression of Nanog and Oct4, which represents stemness factors, and the expression of Runx2, which represents differentiation factors, were increased.

[Example 7] Preparation of Muscle Stem Cell Expressing Lin28 Using Viral Vector

A muscle stem cell-specific progenitor cell was isolated from Hsd:ICR(CD-1) and cultured. During the initial period of the culture, the muscle stem cell-specific progenitor cell was proliferated and cultured after introducing a doxycycline-inducible lentiviral vector inducing the expression of Lin28 into the cell using Lin28 of SEQ ID No. 2. During the proliferation and culture, a muscle stem cell-specific progenitor cell expressing Lin28 was prepared by adding doxycycline thereto and inducing the expression of the Lin28 gene in the muscle stem cell-specific progenitor cell.

[Experimental Example 13] Identification of Muscle Cell Properties of Muscle Stem Cell-Specific Progenitor Cell Expressing Lin28

For the muscle stem cell-specific progenitor cell prepared in Example 6, the degree of expression of MyoD, which is a muscle cell-specific factor in the 2rd passage and the 4th passage, was identified through real-time PCR after the introduction of Lin28, and the number of muscle stem cell-specific progenitor cells was measured.

In FIG. 16, it was confirmed that after Lin28 was introduced into the cell in the 2rd passage, the expression of FHL1, MyoD, Myogenin, and PAX7, which are muscle cell-specific factors, in the 2rd passage and the 4th passage was increased (B). Further, in FIG. 16C, it was confirmed that after the expression of Lin28 was induced, an increase in the number of muscle stem cell-specific progenitor cells was caused.

In addition, as illustrated in FIG. 17, the number of muscle stem cell-specific progenitor cell was increased after the 6th passage. In FIG. 18, it was confirmed that differentiation of muscles was promoted.

[Example 8] Preparation of Nestin-Specific Lin28a Knock Outed Mouse

Heterozygous Lin28a and Lin28b floxed mouse (The Jackson Laboratory, Stock No. 023915) were crossed with pNestin-Cre heterozygous transgenic mice (The Jackson laboratory, Stock No. 003771) to generate a double-conditional Lin28a/b knock outed mutant. All procedures for animal experiments were approved by the Institutional Animal Care and Use Committee (IACUC) at Hanyang College of Medicine with the approval number (2017-0056) Animals were housed in a specific pathogen-free barrier facility with a 12-h light/dark cycle and maintained on standard chow (5053 PicoLabR Rodent Diet 20).

[Experimental Example 14] Identification of the Body Weight, the Amount of Muscle and Muscle Fibrosis in Mouse Model that Knocked Out Lin28 Gene 1) Mouse Skeletal Muscle Myoblast Isolation, Culture, and Differentiation Young (4 weeks old) BL6 mice were sacrificed using CO2 asphyxiation and the muscles in the hind limbs were exposed by cutting the skin. Tibialis anterior (TA), extensor digitorum longus (EDL), and gastrocnemius muscle (GE) muscles were excised from the bone by cutting the tendons. Isolated muscles were then mixed together by being minced in the F-10 media using a surgical blade. Minced muscle was then incubated in the Collagenase IV/Dispase mixture to release skeletal muscle myoblast from the tissue. Tissue slurry was then strained using a 40 μm strainer and serially plated twice into a non-coated culture dish for one hour each to remove fibroblastic cells. Unadherent cells were then collected and cultured in the collagen coated culture dishes using F-10 media supplemented with 20% FBS and 20 ng/ml bFGF along with intermittent media change. Myoblast was passaged when the plate reached 50% confluency. For inducing muscle differentiation, nearly confluent myoblast was plated on a matrigel coated dish. Myogenic differentiation was induced by reduction of serum to a minimum and removal of bFGF (DMEM, 2% HS). The differentiation potential of the myoblast was monitored using MF20 (myosin heavy chain) immunostaining and calculating the fusion index.

2) Muscle Section Immunofluorescence Staining

TA or GE muscles were isolated from the sacrificed mice in a similar fashion as described above, by taking caution not to touch or stretch the muscles. Isolated muscles were weighed and snap frozen by immersing isopentane that is placed inside liquid nitrogen bath for several seconds depending on the muscle size. The frozen muscles were stored in −80° C. until use. Frozen muscles were fixed on a cryosection stage by placing them on top of OCT. For staining, a 6-15μm section was used and all analyzed images were obtained from the midbelly part of the muscle.

As illustrated in FIG. 19, it could be confirmed that the stemness properties were decreased through decrease of Pax7, which is a marker of muscle stem cells, and the amount of muscle was reduced because differentiation into TA muscle and GE muscle was decreased. Moreover, in FIGS. 20 and 21, muscular fibrosis, which is a marker of muscle aging, was observed in the TA muscle and GE muscle.

[Example 9] Preparation of Epithelial Progenitor Cell Expressing Lin28 Using Viral Vector An epithelial progenitor cell was isolated from Hsd:ICR (CD-1) and cultured. During the initial period of the culture, the epithelial progenitor cell was proliferated and cultured after introducing a doxycycline-inducible lentiviral vector inducing the expression of Lin28 into the cell using Lin28 of SEQ ID No. 2. During the proliferation and culture, an epithelial stem cell expressing Lin28 was prepared by adding doxycycline thereto and inducing the expression of the Lin28 gene in the epithelial progenitor cell.

[Experimental Example 15] Identification of Epithelial Progenitor Cell Properties of Epithelial Progenitor Cell Expressing Lin28

After Lin28 was introduced into the epithelial progenitor cell in the 2rd passage, epithelial progenitor cell properties according to the proliferation of the passage were identified.

In FIG. 22, it was observed that after Lin28 was introduced, an increase in the number of epithelial progenitor cells is caused in experimental groups (L3, L5, and L7) in which Lin28 was expressed as proliferation progressed in the 3rd, 5th, and 7th passages (A). Further, through the fact that during the 3rd, 5th, and 7th passaging, the expression of P16, P21, and P53, which are apoptotic cell death factors, and Vimentin, Desmin, and SMA, which are epithelial progenitor differentiation factors, was decreased, it could be confirmed that epithelial progenitor cell properties thereof were maintained (B).

[Experimental Example 16] Identification of Stem Cell Properties of Umbilical Cord-Derived Hematopoietic Stem Cell Expressing Lin28

The stemness properties of human Umbilical cord-derived hematopoietic stem cells was identified.

As illustrated in FIG. 23, it could be confirmed that the stemness properties represented by CD34 was maintained in umbilical cord hematopoietic stem cells in which Lin28 expression was induced.

[Experimental Example 17] Genetic Analysis of Induction of Expression of Lin28

RNA was isolated from tissues or cells by using a Trizol reagent, followed by isopropanol precipitation. For RNA-seq analysis, the quality of RNA was checked by using a Bioanalyzer to ensure intact RNA preparation was utilized.

RNA sequencing analysis was performed to analyze the cause of the effect of the expression of Lin28 at the genetic level. As illustrated in FIG. 24, it was confirmed that the efficiency of protein expression was increased and the regeneration ability was improved through regulation of genes and reduction of inflammation.

REFERENCES

1. Cimadamore F, et al. "SOX2-LIN28/let7 pathway regulates proliferation and neurogenesis in neural precursors." Proc Natl Acad Sci USA. 2013 August 6; 110(32):E3017-26. (published on Aug. 6, 2013)
2. Mei Yang, et al. "Lin28 promotes the proliferative capacity of neural progenitor cells in brain development." Development 2015 142:1616-1627. (Published in 2015)

The invention claimed is:

1. A method for preparing a neural stem cell in which the loss of renewal ability and differentiation potency of the neural stem cell during a subculture of the neural stem cell is blocked, comprising the step of subculturing the neural stem cell into which a vector expressing Lin28 has been introduced, wherein the vector is an adenovirus vector or an RNA replicon, and wherein the step of subculturing the neural stem cell limits the expression of Lin28 in the neural stem cell into which Lin28 has been introduced to within two weeks during the proliferation period of the neural stem cell by adding doxycycline which induces the expression of Lin28.

* * * * *

SEQUENCE LISTING

```
<160> NUMBER OF SEQ ID NOS: 2

<210> SEQ ID NO 1
<211> LENGTH: 4024
<212> TYPE: DNA
<213> ORGANISM: Homo sapiens

<400> SEQUENCE: 1
caccgctatt gtgcggggga agatgtagca gcttcttctc cgaaccaacc ctttgccttc      60
ggacttctcc ggggccagca gccgcccgac caggggcccg gggccacggg ctcagccgac     120
gaccatgggc tccgtgtcca accagcagtt tgcaggtggc tgcgccaagg cggcagaaga     180
ggcgcccgag gaggcgccgg aggacgcggc ccgggcggcg gacgagcctc agctgctgca     240
cggtgcgggc atctgtaagt ggttcaacgt gcgcatgggg ttcggcttcc tgtccatgac     300
```

-continued

```
cgcccgcgcc ggggtcgcgc tcgacccccc agtggatgtc tttgtgcacc agagtaagct      360
gcacatggaa gggttccgga gcttgaagga gggtgaggca gtggagttca cctttaagaa      420
gtcagccaag ggtctggaat ccatccgtgt caccggacct ggtggagtat tctgtattgg      480
gagtgagagg cggccaaaag gaaagagcat gcagaagcgc agatcaaaag gagacaggtg      540
ctacaactgt ggaggtctag atcatcatgc caaggaatgc aagctgccac cccagcccaa      600
gaagtgccac ttctgccaga gcatcagcca tatggtagcc tcatgtccgc tgaaggccca      660
gcagggccct agtgcacagg gaaagccaac ctactttcga gaggaagaag aagaaatcca      720
cagccctacc ctgctcccgg aggcacagaa ttgagccaca tgggtgggg ctattcttt       780 tgctatcagg aagttttgag gagcaggcag agtggagaaa gtgggaatag ggtgcattgg     840
ggctagttgg cactgccatg tatctcaggc ttgggttcac accatcaccc tttcttccct     900
ctaggtgggg ggaaagggtg agtcaaagga actccaacca tgctctgtcc aaatgcaagt     960
gagggttctg ggggcaacca ggaggggga atcaccctac aacctgcata ctttgagtct      1020
ccatccccag aatttccagc ttttgaaagt ggcctggata gggaagttgt tttccttta      1080 aagaaggata tataataatt cccatgccag agtgaaatga ttaagtataa gaccagattc     1140
atggagccaa gccactacat tctgtggaag gagatctctc aggagtaagc attgtttttt     1200
tttcacatct tgtatcctca tacccacttt tgggataggg tgctggcagc tgtcccaagc     1260
aatgggtaat gatgatggca aaagggtgt ttggggaac agctgcagac ctgctgctct       1320
atgctcaccc ccgccccatt ctgggccaat gtgattttat ttatttgctc ccttggatac    1380
tgcaccttgg gtcccacttt ctccaggatg ccaactgcac tagctgtgtg cgaatgacgt    1440
atcttgtgca ttttaacttt ttttccttaa tataaatatt ctggttttgt attttttgtat  1500 attttaatct aaggccctca tttcctgcac tgtgttctca ggtacatgag caatctcagg    1560
gatagccagc agcagctcca ggtctgcgca gcaggaatta cttttttgttg ttttttgccac  1620 cgtggagagc aactatttgg agtgcacagc ctattgaact acctcatttt tgccaataag    1680
agctggcttt tctgccatag tgtcctcttg aaaccccctc tgccttgaaa atgttttatg    1740
ggagactagg ttttaactgg gtggccccat gacttgattg ccttctactg gaagattggg    1800
aattagtcta acaggaaat ggtggtacac agaggctagg agaggctggg cccggtgaaa      1860
aggccagaga gcaagccaag attaggtgag ggttgtctaa tcctatggca caggacgtgc    1920
tttacatctc cagatctgtt cttcaccaga ttaggttagg cctaccatgt gccacagggt    1980
gtgtgtgtgt ttgtaaaact agagttgcta aggataagtt taaagaccaa tacccctgta    2040
cttaatcctg tgctgtcgag ggatggatat atgaagtaag gtgagatcct taacctttca    2100
aaattttcgg gttccaggga gacacacaag cgagggtttt tgtggtgcctg gagcctgtgt   2160 cctgccctgc tacagtagtg attaatagtg tcatggtagc taaaggagaa aaagggggtt    2220
tcgtttacac gctgtgagat caccgcaaac ctaccttact gtgttgaaac gggacaaatg    2280
caatagaacg cattgggtgg tgtgtgtctg atcctgggtt cttgtctccc ctaaatgctg    2340 cccccccaagt tactgtattt gtctgggctt tgtaggactt cactacgttg attgctaggt   2400
ggcctagttt gtgtaaatat aatgtattgg tctttctccg tgttctttgg gggttttgtt   2460
tacaaacttc ttttttgtatt gagagaaaaa tagccaaagc atctttgaca gaaggttctg  2520
caccaggcaa aaagatctga aacattagtt tgggggcccc tcttcttaaa gtggggatct   2580
tgaaccatcc tttcttttgt attccccttc ccctattacc tattagacca gatcttctgt   2640
```

```
cctaaaaact tgtcttctac cctgccctct tttctgttca ccccaaaag aaaacttaca    2700 cacccacaca catacacatt tcatgcttgg agtgtctcca caactcttaa atgatgtatg    2760
caaaaatact gaagctagga aaaccctcca tcccttgttc ccaacctcct aagtcaagac    2820
cattaccatt tctttctttc tttttttttt tttttaaaa tggagtctca ctgtgtcacc    2880
caggctggag tgcagtggca tgatcggctc actgcagcct ctgcctcttg ggttcaagtg    2940
attctcctgc ctcagcctcc tgagtagctg ggatttcagg cacccgccac actcagctaa    3000
tttttgtatt tttagtagag acggggtttc accatgttgt ccaggctggt ctggaactcc    3060
tgacctcagg tgatctgccc accttggctt cccaaagtgc tgggattaca ggcatgagcc    3120
accatgctgg gccaaccatt tcttggtgta ttcatgccaa acacttaaga cactgctgta    3180
gcccaggcgc ggtggctcac acctgtaatc ccagcacttt ggaaggctga ggcgggcgga    3240
tcacaaggtc acgagttcaa aactatcctg gccaacacag tgaaaccccg tctctactaa    3300
aatacaaaaa aattagccgg gtgtggtggt gcatgccttt agtcctagct attcaggagg    3360
ctgaggcagg ggaatcgctt gaacccgaga ggcagaggtt gcagtgagct gagatcgcac    3420
cactgcactc cagcctggtt acagagcaag actctgtctc aaacaaaaca aaacaaaaca    3480
aaaacacact actgtatttt ggatggatca aacctcctta attttaattt ctaatcctaa    3540
agtaaagaga tgcaattggg ggccttccat gtagaaagtg gggtcaggag gccaagaaag    3600
ggaatatgaa tgtatatcca agtcactcag gaacttttat gcaggtgcta gaaactttat    3660
gtcaaagtgg ccacaagatt gtttaatagg agacgaacga atgtaactcc atgtttactg    3720
ctaaaaacca aagctttgtg taaaatcttg aatttatggg gcgggagggt aggaaagcct    3780
gtacctgtct gttttttttcc tgatccttt ccctcattcc tgaactgcag gagactgagc    3840 cccttgggc tttggtgacc ccatcactgg ggtgtgttta tttgatggtt gattttgctg    3900
tactgggtac ttccttccc attttctaat catttttaa cacaagctga ctcttccctt    3960
cccttctcct ttccctggga aaatacaatg aataaataaa gacttattgg tacgcaaact    4020
gtca                                                                4024
```

```
<210> SEQ ID NO 2
<211> LENGTH: 3480
<212> TYPE: DNA
<213> ORGANISM: Mus musculus

<400> SEQUENCE: 2
cctttgcctc cggacttctc tggggccagc agccgcccga cctggggccc ggggccacgg      60
gctcagcaga cgaccatggg ctcggtgtcc aaccagcagt ttgcaggtgg ctgcgccaag     120
gcagcggaga aggcgccaga ggaggcgccg cctgacgcgg cccgagcggc agacgagccg     180
cagctgctgc acggggccgg catctgtaag tggttcaacg tgcgcatggg gttcggcttc     240
ctgtctatga ccgcccgcgc tggggtcgcg ctcgaccccc cggtggacgt ctttgtgcac     300
cagagcaagc tgcacatgga aggttccga agcctcaagg agggtgaggc ggtggagttc     360
acctttaaga agtctgccaa gggtctggaa tccatccgtg tcactggccc tggtggtgtg     420
ttctgtattg ggagtgagcg gcggccaaaa gggaagaaca tgcagaagcg aagatccaaa     480
ggagacaggt gctacaactg cggtgggcta gaccatcatg ccaaggaatg caagctgcca     540
ccccagccca agaagtgcca cttttgccaa agcatcaacc atatggtggc ctcgtgtcca     600
ctgaaggccc agcagggccc cagttctcag ggaaagcctg cctacttccg ggaggaagag     660
gaagagatcc acagccctgc cctgctccca gaagcccaga attgaggccc aggagtcagg     720
```

```
gttattctttt ggctaatggg gagtttaagg aaagaggcat caatctgcag agtggagaaa       780 gtggggtaa gggtgggttg cgtgggtagc ttgcactgcc gtgtctcagg ccggggttcc         840
cagtgtcacc ctgtctttcc ttggagggaa ggaaaggatg agacaaagga actcctacca       900
cactctatct gaaagcaagt gaaggctttt gtggggagga accaccctag aacccgaggc       960
tttgccaagt ggctgggcta gggaagttct tttgtagaag gctgtgtgat atttcccttg      1020
ccagacggga agcgaaacaa gtgtcaaacc aagattactg aacctacccc tccagctact      1080
atgttctggg gaagggactc ccaggagcag ggcgaggtta ttttcacacc gtgcttattc      1140
ataaccctgt cctttggtgc tgtgctggga atggtctcta gcaacgggtt gtgatgacag      1200
gcaaagaggg tggttgggga gacaactgct gacctgctgc ccacacctca ctcccagccc      1260
tttctgggcc aatgggattt taatttattt gctcccttag gtaactgcac cttgggtccc      1320
actttctcca ggatgccaac tgcactatct acgtgcgaat gacgtatctt gtgcgttttt      1380
ttttttttta attttaaaa tttttttca tcttcttaat ataaataatg ggtttgtatt        1440
tttgtatatt ttaatcttaa ggccctcatt cctgcactgt gttctcaggt acatgagcaa      1500
tctcagggat aataagtccg tagcagctcc aggtctgctc agcaggaata ctttgttttg      1560
ttttgttttg atcaccatgg agaccaacca tttggagtgc acagcctgtt gaactacctc      1620 attttttgccg attacagctg gcttttctgc catagcgtcc ttgaaaaatg tgtctcacgg     1680
gtttcgattg agctgcccca agacttgatc tggatttggc aaaacatagg acatcactct      1740
aaacaggaaa gggtggtaca gagacattaa aaggctgggc caggtgaaag gcacaagagg      1800
aactttccat accagatcca tccttttgcc agattagtgg aagcctgcca tgcacagcag      1860
ggtgtgagag agagagtgtg tatgtatgtg tgtgtggatt tttttttaatg caaatttatg     1920 aagacgaggt gggttttgtt tatttgattg cttttttgtgc tggggatgga atcttgggct     1980
tcatttgtgc taggaagtac actgccactg agttatccca gtaagaatgc aacttaagac      2040 cagtacccctt attcccacac tgtgctgtcc aggcatggga acatgaggca gggactcaac    2100
tccttagcct ttcacaatct tggctttctg agagactcat gagtatgggc ctcagtggca     2160
agtgtcctgc cctgctgtag cgtgatggtt gatagctaaa ggaaagaggg ggtggggagt    2220
ttcgtttaca tgctttgaga tcgccacaaa cctacctcac tgtgttgaaa cgggacaaat    2280
gcaatagaac acattgggtg gtgtgtgtgt gtgtctgatc ttggtttctt gtctccctct     2340
ccccccaaat gctgccctca cccctagtta attgtattcg tctggccttt gtaggacttt    2400
tactgtctct gagttggtga ttgctaggtg gcctagttgt gtaaatataa atgtgttggt    2460
cttcatgttc ttttggggtt ttattgtttta caaaacttttt gttgtattga gagaaaaata  2520
gccaaagcat ctttgacaga aagctctgca ccagacaaca ccatctgaaa cttaaatgtg    2580
cggtcctctt ctcaaagtga acctctggga ccatggctta tccttacctg ttcctcctgt    2640
gtctcccatt ctggaccaca gtgaccttca gacagcccct cttctccctc gtaagaaaac    2700
ttaggctcat ttacttcttt gagcatctct gtaactcttg aaggacccat gtgaaaattc    2760
tgaagaagcc aggaacctca ttctttcctt gtccctaact cagtgaagag ttttggttgg    2820
tggttttgag acagggcctc actctgtagc tggagataga gagcctcggg ttcctggctc    2880
tcctcctgcc ttctgcacag agtcccctgt gcagggattg caggtgccgc ttctccctgg    2940
caagaccatt tatttcatgg tgtgattcgc ctttggatgg atcaaaccaa tgtaatctgt    3000 caccccttagg tcgagagaag caattgtggg gccttccatg tagaaagttg gaatctggac  3060
```

```
accagaaaag ggactatgaa tgtacagtga gtcactcagg aacttaatgc cggtgcaaga    3120
aacttatgtc aaagaggcca caagattgtt actaggagac ggacgaatgt atctccatgt    3180
ttactgctag aaaccaaagc tttgtgagaa atcttgaatt tatggggagg gtgggaaagg    3240
gtgtacttgt ctgtcctttc cccatctctt tcctgaactg caggagacta aggccccca    3300 cccccgggg cttggatgac ccccacccct gcctggggtg ttttatttcc tagttgattt    3360
ttactgtacc cgggcccttg tattcctatc gtataatcat cctgtgacac atgctgactt    3420
ttccttccct tctcttccct gggaaaataa agacttattg gtactccaga gttggtactg    3480
```